US012612668B2

(12) United States Patent
Buyyarapu et al.

(10) Patent No.: US 12,612,668 B2
(45) Date of Patent: Apr. 28, 2026

---

(54) SNP MARKERS AND SELECTION OF LOW FIBER IN BRASSICA

(71) Applicant: Agrigenetics, Inc., Indianapolis, IN (US)

(72) Inventors: Ramesh Buyyarapu, Waukee, IA (US); Thomas G. Patterson, Westfield (IN); Ryan L. Preuss, Clive, IA (US); Siva S. Ammiraju Jetty, Johnston, IA (US); Van L. Ripley, Grandora (CA); Syed Masood Rizvi, Indianapolis, IN (US); Steve Rounsley, Waukee, WI (US); Muhammad Tahir, Saskatoon (CA)

(73) Assignee: AGRIGENETICS, INC., Indianapolis, IN (US)

( * ) Notice: Subject to any disclaimer, the term of this patent is extended or adjusted under 35 U.S.C. 154(b) by 435 days.

(21) Appl. No.: 17/415,290

(22) PCT Filed: Dec. 13, 2019

(86) PCT No.: PCT/US2019/066135
§ 371 (c)(1),
(2) Date: Jun. 17, 2021

(87) PCT Pub. No.: WO2020/131600
PCT Pub. Date: Jun. 25, 2020

(65) Prior Publication Data
US 2022/0017975 A1      Jan. 20, 2022

Related U.S. Application Data

(60) Provisional application No. 62/782,699, filed on Dec. 20, 2018.

(51) Int. Cl.
*C12Q 1/68* (2018.01)
*A01H 1/04* (2006.01)
*A01H 6/20* (2018.01)
*C12Q 1/6895* (2018.01)

(52) U.S. Cl.
CPC ........... *C12Q 1/6895* (2013.01); *A01H 1/045* (2021.01); *A01H 6/202* (2018.05); *C12Q 2600/13* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 9,066,483 B2 | 6/2015 | Chungu et al. | |
| 9,702,013 B2 | 7/2017 | Falak et al. | |
| 10,791,692 B2 | 10/2020 | Tang et al. | |
| 11,713,490 B2 | 8/2023 | Tang et al. | |
| 2010/0303999 A1 | 12/2010 | Chungu et al. | |

| | | | |
|---|---|---|---|
| 2014/0220564 A1 | 8/2014 | Zhang et al. | |
| 2016/0100619 A1 | 4/2016 | Patterson et al. | |
| 2017/0332593 A1* | 11/2017 | Tang ................... | C12Q 1/6895 |

FOREIGN PATENT DOCUMENTS

| | | |
|---|---|---|
| CA | 2678954 | 8/2008 |
| CN | 101962640 A | 2/2011 |
| CN | 102021235 A | 4/2011 |
| CN | 102226189 A | 10/2011 |
| CN | 102703438 A | 10/2012 |
| CN | 102226189 | 11/2012 |
| CN | 101962640 | 3/2013 |
| CN | 102021235 | 3/2013 |
| CN | 102703438 | 11/2013 |
| EP | 3234197 A1 | 10/2017 |
| WO | 2007016521 A2 | 2/2007 |
| WO | 2016100883 | 6/2016 |

OTHER PUBLICATIONS

Badani et al. 2006 (Genome December: vol. 49 No. 12 pp. 1499-1509) (Year: 2006).*
Badani et al 2006 (Genome 6: p. 1499-1509) (Year: 2006).*
Akhov et al., "Proanthycyanidin biosynthesis in the seed coat of yellow-seeded, canola quality *Brassica-opus* YN001-29 is constrained at the committed step catalyzed by dihydroflavonon 4-reductase," Botany + Botanique, Jun. 2009, pp. 616-625, vol. 87, No. 6.
Badani et al., "Colocalization of a partially dominant gene for yellow seed color with a major QTL influencing acid detergent fibre (ADF) content in different crosses of oilseed rape (*Brassica napus*)," Genome, 2006, pp. 1499-1509, vol. 49.
"Infinium Assay Workflow," Illumina, <http://www.bea.ki.se/documents/workflow_infinium.pdf>, Oct. 11, 2012, 2 pages.
International Search Report and Written Opinion for PCT/US2019/066135.
Liu et al., "A high-density SNP map for accurate mapping of seed fibre QTL in *Brassica napus* L.," PLoS One, 2013, pp. 1-9, vol. 8, Issue 12.
Nesi et al., "Genetic and molecular approaches to improve nutritional value of *Brassica napus* L. seed," Comptes Rendus Biologies, 2008, pp. 763-771, vol. 331.

(Continued)

*Primary Examiner* — Matthew R Keogh

(57)      ABSTRACT

This disclosure concerns methods and compositions for identifying canola plants that have a low fiber content trait. Some embodiments concern a chromosomal interval and a quantitative trait locus associated with low fiber content in canola plants or germplasm. Some embodiments concern molecular markers to identify, select, and/or construct low fiber content canola plants and germplasm, or to identify and counter-select plants with relatively higher fiber content. This disclosure also concerns canola plants comprising a low fiber content trait that are generated by methods utilizing at least one marker described herein.

11 Claims, 1 Drawing Sheet
Specification includes a Sequence Listing.

(56) References Cited

OTHER PUBLICATIONS

Relf-Eckstein, et al., Meal quality improvement in *Brassica napus* canola through the development of low fibre ; (yellow-seeded) germplasm; Feed and Industrial Raw Material: pp. 289-291 (2007).

NCBI GenBank Accession XM_009119363_Predicted: *Brassica rapa* 2-isopropylmalate synthase 1, chloroplastic (LOC103842698), mRNA, published Oct. 13, 2016.

NCBI GenBank Accession XM_009119508_Predicted: *Brassica rapa* post-GPI attachment to proteins factor 3 (LOC103842843), transcript variant X2, mRNA, published Oct. 13, 2016.

NCBI GenBank Accession LR031872: "*Brassica oleracea* HDEM genome, scaffold: C3", Nov. 16, 2018 (Nov. 16, 2018)—partial entry with alignment as cited by International Search Report and Written Opinion for PCT/US2019/066135.

Rakow et al. "Rapeseed genetic research to improve its agronomic performance and seed quality" Helia, 2007, pp. 199-206, vol. 30, No. 46.

Batista C., et al., "Nutritional and Nutraceutical Potential of Rape (*Brassica napus* L. Var. *Napus*) and "Tronchuda" Cabbage (*Brassica oleraceae* L. Var. *Costata*) Inflorescences," 2011, Food and Chemical Toxicology, vol. 49, pp. 1208-1214.

Chalhoub B., et al., "Early Allopolyploid Evolution in the Post-Neolithic *Brassica napus* Oilseed Genome," Aug. 22, 2014, Science, vol. 345, No. 6199, pp. 950-953, 6 Pages.

Clarke W.E., et al., "A High-Density SNP Genotyping Array for *Brassica napus* and its Ancestral Diploid Species Based on Optimised Selection of Single-locus Markers in the Allotetraploid Genome," Theoretical and Applied Genetics, 2016, vol. 129, No. 10, pp. 1887-1899, Supplementary Table 1 of Clarke et al.

Clarke W.E., et al., "Genomic DNA Enrichment Using Sequence Capture Microarrays: A Novel Approach to Discover Sequence Nucleotide Polymorphisms (SNP) in *Brassica napus* L", PLOS One, 2013, vol. 8, No. 12, pp. 1-14, XP055834905.

Declaration of Snowdon R.J., EP Opposition No. 3234197B1, dated Jul. 26, 2021, Submitted in Opposition of EP3234197B1 on Aug. 9, 2021, 2 Pages.

Edwards D., et al., "Accessing Complex Crop Genomes with Next-Generation Sequencing," Theoretical and Applied Genetics, 2012, 2013, vol. 126, pp. 1-11.

EP Opposition EP3234197B1_Cited Document D18_Alignment of Sequence rs# 21212 of Wang et al. 2016 8 with SEQ ID Nos. 14-17 of the Patent Highlighting Relevant SNPs, Submitted on Jan. 2, 2022.

EP Opposition EP3234197B1—Cited Document D10 Alignment of Selected Sequences in *Brassica napus* 60K Illumina Infinium TM SNP Array and EP3234197B1,7 Pages.

EP Opposition EP3234197B1—Cited Document Maiwald D7b Alignment of Selected Sequences of Opposed Patent in SRX377527 and EP3234197B1, 14 Pages.

EP Opposition No. EP3234197B_Cited Document D15_p. 7 of Amendment filed for U.S. Appl. No. 15/731,561 dated Apr. 29, 2020.

Extended European Search Report for European Application No. 15871207.5, mailed May 15, 2018, 10 Pages.

Extended European Search Report for European Application No. 19899942.7, mailed Aug. 11, 2022, 7 Pages.

Extended European Search Report for European Application No. 20206561.1, mailed May 10, 2021, 9 Pages.

International Preliminary Report on Patentability for International Application No. PCT/US2015/066813, mailed Jun. 29, 2017, 8 Pages.

International Preliminary Report on Patentability for International Application No. PCT/US2019/066135, mailed Jul. 1, 2021, 9 Pages.

International Search Report and Written Opinion for International Application No. PCT/US2015/066813, mailed Apr. 11, 2016, 12 Pages.

Liu L.Z., et al., "QTL Mapping for Seed Coat Color of *Brassica oleracea* (English)," Acta Genetic Sinica 1-27 *, pp. 181-187, Feb. 2006.

McEntyre J., et al., "Chapter 5: The Single Nucleotide Polymorphism Database (dbSNP) of Nucleotide Sequence Variation," by Adrienne Kitts, The NCBI Handbook [Internet] Bethesda (MD): National Center for Biotechnology Information (US), Created on Oct. 9, 2002, 25 Pages, Last Updated Feb. 2, 2011.

NCBI: "*Brassica napus* Strain DH12075 (rape)," *Brassica napus* Strain: DH12075 Targeted Locus (Loci), Submitted on Sep. 11, 2013,1 Page.

NCBI Genbank: "Predicted *Brassica rapa* Post-GPI Attachment to Proteins Factor 3-like (LOC103842843), Transcript Variant X1 Sequence," NCBI/GenBank accession No. XM_009119508, Published on Oct. 13, 2016.

NCBI: "SRX377527, YN429 Sequence Capture," Jul. 17, 2014, 1 Page.

Nelson S.C., et al., "Is 'Forward' the Same as 'Plus' ?. . . and Other Adventures in SNP Allele Nomenclature," Trends in Genetics, Aug. 2012, vol. 28, No. 8, pp. 361-363, 6 Pages.

Notice of Opposition Submitted in European Patent Office for EP3234197B1, dated Aug. 9, 2021,45 Pages.

Opposition of EP3234197B1_Cited Document Maiwald D8a Alignment of Selected Sequences in ROW 84 of Table S4 of Wang et al. 2015 and EP3234197B1, Submitted on Aug. 9, 2021, 2 Pages.

Oraby H.F., et al., "Impact of Suppressing the Caffeic Acid O—Methyltransferase (COMT) Gene on Lignin, Fiber, and Seed Oil Composition in *Brassica napus* Transgenic Plants," European Food Research and Technology, Published on Dec. 4, 2014, 2015, vol. 240, pp. 931-938, DOI: 10.1007/s00217-014-2397-3, XP055834900.

Response to Notice of Opposition in European Patent Office for EP3234197B1, dated Jan. 2, 2022,16 Pages.

Shoaib M., et al., "Dry Matter Yield and Forage Quality of Oat, Barley and Canola Mixture," Pakistan Journal of Agricultural Sciences, 2014, vol. 51, No. 2, pp. 443-449.

Slominski B.A., et al., "Low-Fiber Canola. Part 1. Chemical and Nutritive Composition of the Meal," Journal of Agricultural and Food Chemistry, 2012, vol. 60, pp. 12225-12230.

Slominski B.A., "Nutritive Value of Canola Meal: The Dietary Fibre Story," University of Manitoba, Jul. 2015, 55 Pages, URL: https://www.agwest.sk.ca/IRC2015/BSlominskiCanolameal.pdf, XP055834548.

Somers D.J., et al., "Identification of a Major Gene and RAPD Markers for Yellow Seed Coat Colour in *Brassica napus*," Genome, 2001, vol. 44, No. 6, pp. 1077-1082.

Wang J., et al., "Genome-Wide Analysis of Seed Acid Detergent Lignin (ADL) and HULL Content in Rapeseed (*Brassica napus* L.)," PLOS One, Dec. 16, 2015, vol. 10, No. 12(e014045), 18 Pages.

Yan et al., "Co-Location of Seed Oil Content, Seed Hull Content and Seed Coat Color QTL in Three Different Environments in *Brassica napus* L," Euphytica, 2009, vol. 170, pp. 355-364, DOI: 10.1007/s10681-009-0006-5, XP019748260.

Ma Z.Z., et al., "QTL Analysis of Oil Content, Protein, Cellulose and Hemicellulose Content in *Brassica napus* Seeds," Acta Crops [Y] 1-27 * 1214-1222.

* cited by examiner

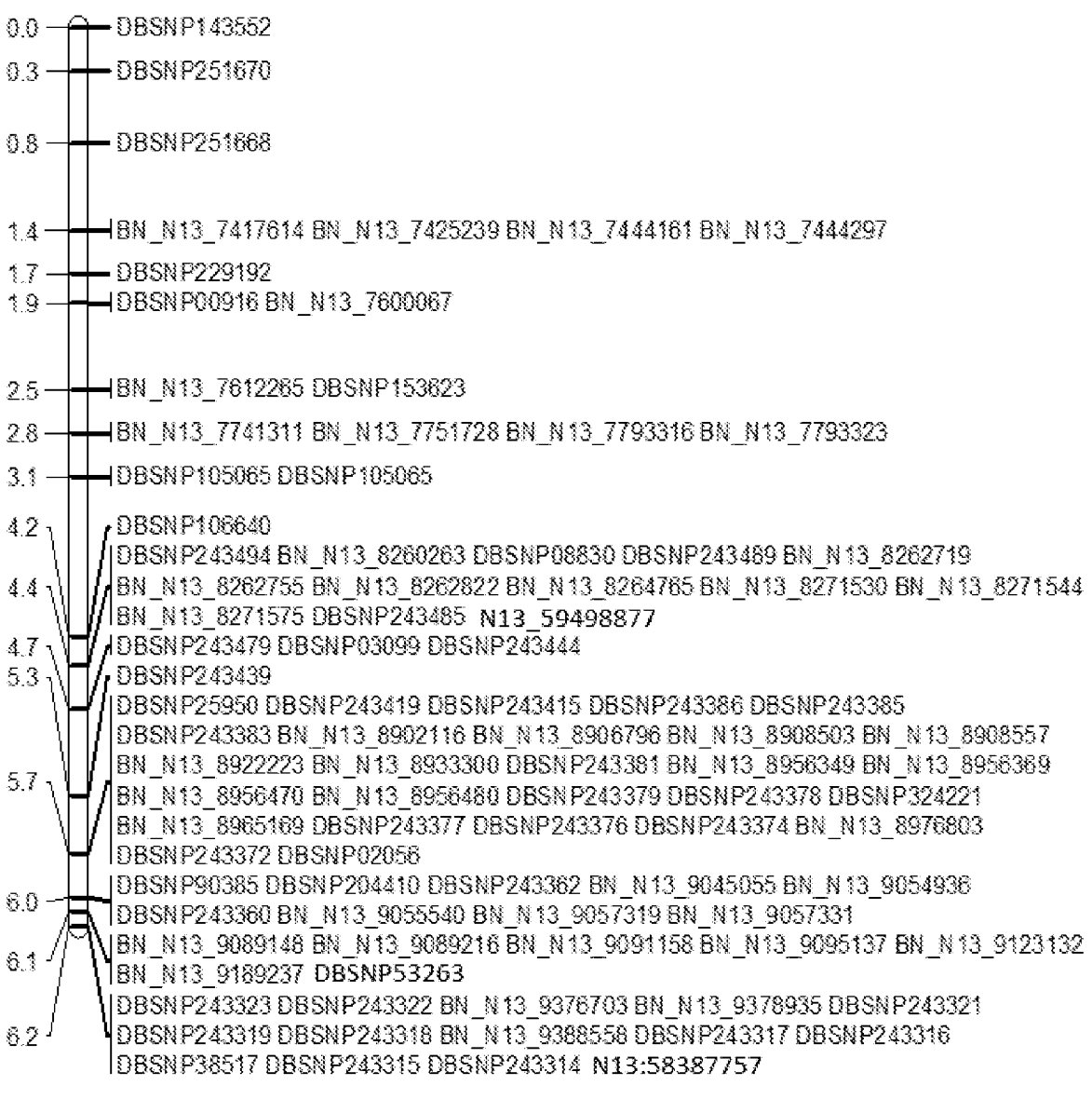

SEQUENCE LISTING

<160> NUMBER OF SEQ ID NOS: 100

<210> SEQ ID NO 1
<211> LENGTH: 520
<212> TYPE: DNA
<213> ORGANISM: Brassica napus

<400> SEQUENCE: 1

```
agcttattag cctcaaaaga agttcttcac aagggtctcc ggaagaagat aggaaatgga      60
catacaacga aagtatggga ggagccctgg ctcccaacgc aaccagcgag agcaccactt     120
agcattgaca acgtctgaga cgaagacttc cgcgttcatc atctaattga tgctcagaat     180
cagtcttgga atctagagat actaaacgca gtcatcgccr cggaggatat tcccaggatt     240
acatcactcc gggtgagccg cacaggtcga catgatagtt acttctggga tttttacgaag    300 tccggagtat actcggtgcg atcaggctac aaaagagccc acgagctcca ctctgcggcc     360
aacccgaacg ttgtaacgga acctagtaca acggaactga agaaagcaac atggaagctc     420
aaagccccat gaaaacttaa acactttcta tggcaagtta caacatgata cctagcgacg     480
gcgaagcaac ttaaagtgag acattgtgct aatgaaagta                           520
```

<210> SEQ ID NO 2
<211> LENGTH: 201
<212> TYPE: DNA
<213> ORGANISM: Brassica napus

<400> SEQUENCE: 2

```
gaaggatgat ttattttttg gcgacataag cacactatat aaaggtcaaa acaccattgt      60
tgatctgaaa atcgacagcc actcaagtgt aagtaaatat mtgtagtgat gcatgctttc     120
tgatcttttg caccttaact gtccttaaac catattaccg aaacgtattt atgcaggtgt     180
cgacaaaagt aactgtcaaa a                                               201
```

<210> SEQ ID NO 3
<211> LENGTH: 121
<212> TYPE: DNA
<213> ORGANISM: Brassica napus

<400> SEQUENCE: 3

```
atggcattgc atgcgttaca tgaaggtagc gagatgtctg aaaccgtttg caattatcca      60
ytatcgtctt agtgcgagaa tcatgtgtgt tctttagagc tttaggtact atagtaatca     120
g                                                                     121
```

<210> SEQ ID NO 4
<211> LENGTH: 301
<212> TYPE: DNA
<213> ORGANISM: Brassica napus

<400> SEQUENCE: 4

-continued

```
ctccgccgtg ggatttgttg aacgatgaga tcatcgatga ggcagcgctt gatcttcgga        60
ccaccacgtg gagctttccg tcgtcaccta tctccgcatc ggtctgatta acaaaacgat       120
gtttttagtc actaggaaat aaaccggaca kaaccaaatt aataaccgaa ccggaagttc       180
aatgccgttt actcgaaatt tctactttgt ccattaatca agctaaatga aagtcaaaat       240
atttctaata agttgatata tatagaaacc caacaacgac atttgattaa ttaagtacta       300
t                                                                      301

<210> SEQ ID NO 5
<211> LENGTH: 301
<212> TYPE: DNA
<213> ORGANISM: Brassica napus

<400> SEQUENCE: 5
atttattggt tgtgtttggt acttagatta tggagttgta ggggttcacc atgtgggtct        60
gctgtgtgaa aacctagaac ggtcactaga gttttaccag aacattctag gccttgagat       120
caacgaggcg aggccacacg ataagcttcc mtatagagga gcatggttat gggtaggttc       180
agagatgatt catctaatgg agcttccaaa tcctgatcca ttaactggta gacccgagca       240
cggtggtcga gatagacatg cttgtatcgc aatccgagat gtttcagttc tgaaagagat       300
t                                                                      301

<210> SEQ ID NO 6
<211> LENGTH: 172
<212> TYPE: DNA
<213> ORGANISM: Brassica napus

<400> SEQUENCE: 6
gtgtcttcca cccttctaaa atatctaccg agtcaaaagt aatacgcacg tgatgcatat        60
tttccaccgt attttgactt tgctggtcta aattctaatc rtacgtcgta cgaggagatt       120
taaataattg tacagtggtc ggttggaata ataactggtt cgaggagca at               172

<210> SEQ ID NO 7
<211> LENGTH: 192
<212> TYPE: DNA
<213> ORGANISM: Brassica napus

<400> SEQUENCE: 7
taactggttt cgaggagcaa ttaatcatac attaacatgg agtatgatct aaacattttc        60
tacatccggc attcatactc aaattmtata tttctatgtg aatctaccgt taagaagagt       120
atgtgtgatt ctattataat tgttctaaca aggtttttttt tttgaattct ttctaactag      180
gttttataaa ac                                                          192

<210> SEQ ID NO 8
<211> LENGTH: 301
<212> TYPE: DNA
<213> ORGANISM: Brassica napus

<400> SEQUENCE: 8
attttctttc ttttggcttg cgtaataaca gaaaaaaccc aacttttttga tcaataaaaa       60 aaaactgtac ataaagaaat tgcttcaatg ttttatgcaa caacataaac aagtcaagaa       120
gctaaaaaag atcaaagctt tttctttatt magagtttat ttgacgagtt tatccaacaa       180
cataagcaac cggccctaaa cacctcgatg cagcaacaaa aaaaacccac caaaaaaact       240
```

-continued

```
cagacgatga aaattttttt tgtcagagat tgcatttgag gatttcatca agcaacaaaa      300
a                                                                        301

<210> SEQ ID NO 9
<211> LENGTH: 451
<212> TYPE: DNA
<213> ORGANISM: Brassica napus

<400> SEQUENCE: 9
tggaagttaa ttttcgcaca aatggaacaa gcgttaaggt taacgttcca gttggtggtg       60
atttgacatt tcacattaac cctgttggcg gactcgtacc acagattgac ggcagattat      120
acgtaaatgg agcccgtgtt tatcctcagg stagcggtgg attcacaata aacgttaacc      180
ctgttgacct gctcgtacct caggctggtg gtggcgtcaa agatgaatat ggatctgaaa      240
accctaaact atctgatcca tctccaggaa tggctaaccc taaggttttc tttgatatga      300
cggtgtgcgg caaaacggtt ggtcggatcg tgatggagct ctttgccgac acgacccac      360 ggacggcaga gaatttccgc gccctctgta caggcgagaa aggcatgggg aagcttggta      420
agccactcca ttacaaagga tcaatcatcc a                                     451

<210> SEQ ID NO 10
<211> LENGTH: 301
<212> TYPE: DNA
<213> ORGANISM: Brassica napus

<400> SEQUENCE: 10
aacggagagt agtattttat tattgggcct tatgcctcct aaaagtatgt tttactatgg       60
gtctatattt ataacctcac gtacctaaaa gctcttaaaa tgttctttac tataaggccc      120
aagaaatctc actgtcaggt ataaatacat rttatcagct ccaaaacct aactctgaga       180 ttagtagatt acgcactcct ttaagcttat tgtagccgtg ggaagaaaaa gcagagaagc      240
aaatcagcag ccatgggtaa tcgtcctcat agtttatagt ataatttgcc attagattga      300
a                                                                        301

<210> SEQ ID NO 11
<211> LENGTH: 301
<212> TYPE: DNA
<213> ORGANISM: Brassica napus

<400> SEQUENCE: 11
ttctacacaa gaaattaaag gaatcaatgg attgaatgct gagcaaaata caggcttttc       60
tttttgatat ctgtccataa ataccggaga taaccgaggg aatattttta aaccgtgctt      120
agactaatgg gttgattaag ggcccattta ratcttacta tgcgcgtctt aatttccgta      180
attatatact aattaatttt cccggtctca cgcgttcaaa ataatatccg ttaccacgaa      240
gaatcgtctt cttctctcca cttctcactt tctctttcta aaaaactgct tatttagaga      300
g                                                                        301

<210> SEQ ID NO 12
<211> LENGTH: 450
<212> TYPE: DNA
<213> ORGANISM: Brassica napus

<400> SEQUENCE: 12
agctttgact cttcacccta tgtgatctcg acacgctgac tcagtcgtta tcgtgcataa       60
gatgtggggg tttcaatgtt taacacttta ctaatattct agtcgcaatc aattcatttt      120
```

-continued

```
gttggacacg atcgttgcaa ctttttatcy tatttattag tttatttcaa aaatattgtg        180
taactaacac gtatgaaaac ccatgcctat cgttaaatcc tgggcatccc attaattcat        240
tactcctctt tttaacaaac taggtgctga gaccccccgc gcaagcgcag agctggttac        300
tttggatatc ggtggggcgg tataatttac ggaatgttgg tgttgtttaa gatttgtgta        360
aattaaaaaa taaaatttat tggaaataag acaacaaaat tgatcctagc ttttgacgat        420
taactcaagt tagagacatc tcccaaaacg                                         450
```

```
<210> SEQ ID NO 13
<211> LENGTH: 301
<212> TYPE: DNA
<213> ORGANISM: Brassica napus

<400> SEQUENCE: 13
cagctctctc aaaggggaac gtggtaataa ttaataaaat ttcttaggtc ttgagacgat         60
aacatattgt tctggtgtca gagagaccgc actttcggat acggtagtgc atggacgtct        120 cttttccacga ttccactcaa aagccaagtt ygttagcttc tcctaggtct acgtagctac       180
atcttatata aaaatgtacc ctaattaata ttttcgttat gtttgtggtc cactaccttc        240
ttcttccttt ttatgattgt tacctctatg gtctttttagg tttaggtcca tagaggaacc       300
t                                                                        301
```

```
<210> SEQ ID NO 14
<211> LENGTH: 301
<212> TYPE: DNA
<213> ORGANISM: Brassica napus

<400> SEQUENCE: 14
tactcttttt accttactat ggttttttcc attgggtttt cctggaaagg ttttttaacga       60 ggcaacaaag acgttaagcg agagcggata gtgacaccgg cccccaaggg gggagtgttac      120 gaaagtcaaa gaaaaaaaag cagcagccac ygcaattgtt gaaaatataa aaatgtgggg       180
cccgttgcac tatttgcaca gtaaatttct ttctatatat acgaacgttt tcgttcattt       240
gtaatcgcac atcaaccttc tcctctctct ataataaact cttcctatca gtgttaaaaa      300
t                                                                        301
```

```
<210> SEQ ID NO 15
<211> LENGTH: 301
<212> TYPE: DNA
<213> ORGANISM: Brassica napus

<400> SEQUENCE: 15
tttccatgca taagtcctta tcaggtgttg gagagagttt catgatgaac tctgtgcccc        60
aaggagtgtt ttgatgccca aagaatgtag atgagtcgtt gaaggatcct agcggccagg       120
cgtagcagca aatgctggtc gctacagaag rtatagcaga aaacctgagg cacccaagta       180
ccatagcggg agtgtgtagc gggctagaga gaccgctagt attgaagcgc tttctacagc       240
ggccagccat agcgacttcg cgaggtcgct atgcgttcaa gacttctaaa atctcccaag       300
t                                                                        301
```

```
<210> SEQ ID NO 16
<211> LENGTH: 301
<212> TYPE: DNA
<213> ORGANISM: Brassica napus
```

-continued

```
<400> SEQUENCE: 16
gcataagtcc ttatcaggtg ttggagagag tttcatgatg aactctgtgc cccaaggagt      60
gttttgatgc ccaaagaatg tagatgagtc gttgaaggat cctagcggcc aggcgtagca     120
gcaaatgctg gtcgctacag aagatatagc wgaaaacctg aggcacccaa gtaccatagc     180
gggagtgtgt agcgggctag agagaccgct agtattgaag cgctttctac agcggccagc     240
catagcgact tcgcgaggtc gctatgcgtt caagacttct aaaatctccc aagtatccta     300
g                                                                     301

<210> SEQ ID NO 17
<211> LENGTH: 519
<212> TYPE: DNA
<213> ORGANISM: Brassica napus

<400> SEQUENCE: 17
atctgttggg gccttttcta gtgattcaat ttgtttaaat ctctttggtt gcactttgat      60
tatatagttg gaatgaaagc tttgctttat ttggttgttc tttttagaat tttcagaagt     120
acatagttaa atcctaaagg catgaaaccc tttcgggcag cactctgtct gcatcaacct     180
taaaacacag gacaaccttt aacgacaaca cctttggcyg tcgggcartg cgctagattg     240
caatggtctg aattctcaag cccccaccaa tcaggcaagc ttacgtcatt gttctgaaac     300
acaaagaata tcaacactcc cataatcgcg gtccctgcat caagcgctgc agagaggatg     360
tagttgtgcc tcgcccacca actcttaaac ctcctgaaga tgtagtagtt gaacacaacc     420
ccaacgatgg tccaggacca atagtgcaca gccttggctt gtggcattga gcttactgca     480
gagaagatca atggaatatg gatgtgtttt agccatttc                           519

<210> SEQ ID NO 18
<211> LENGTH: 750
<212> TYPE: DNA
<213> ORGANISM: Brassica napus

<400> SEQUENCE: 18
atctgttgct gctctttttg ttttttttttg gtcaaatttc aggaaatctt agctatgagt      60
atccatatga ttagcaggac tgttcgcaga aattcaatag gagtggcgtt catatgtgca     120
tgtgacaaac gcattggtgc tcaagtcttc cggaacaagc tattcttcat tcttgttagt     180
tcagagatta atcttgtgat gctgttgaat gggttggaga agaaggaatg gaagtgacag     240
tggtttgtcy gcattgccat agcggatgca aatacaaagg caccgctggt tctaggacat     300
ttcacgttat tagctgagtt tgttttgtg taatatgctt ttattactat aaaaaaagct     360
caatgtttgt ttagtatgct tagaaaacaa tcaaaaactt ttgtgtgttt ggatcttttg     420
tatatttttg tttggataac aatcaaaata tgataatgtc cccaacattt gcacatcaca     480
caaaacaagc tgtcagctaa atcaatgttt acctagtgca tggtagattg atgagcctaa     540
tgcaattgtc accaagggcg tattggttat gctgcatagt gactgagtta agttaagaac     600
caccaaaaac aaatccacaa gagatcaagt taagagacgt tattattgtt ctgtttttcat     660 ggtttggaga tgtaattgtt tatcattgac aatggaattt tggaaagaaa aaagcccatt     720
cattatttgg gaattagact tgggacttaa                                     750

<210> SEQ ID NO 19
<211> LENGTH: 121
<212> TYPE: DNA
<213> ORGANISM: Brassica napus
```

-continued

```
<400> SEQUENCE: 19
ggttttatat aactttartt ttcatgaaat tgtatttcgt tragtttttc gggaaaaatt      60
rtacaaagct attttcagca tcttttatct ttaattaatc gtcgttaagt tmggcatggt     120
g                                                                    121

<210> SEQ ID NO 20
<211> LENGTH: 301
<212> TYPE: DNA
<213> ORGANISM: Brassica napus

<400> SEQUENCE: 20
atgtggtgta atcttttaca tttcttacct taaaaaggga ttcagtacat ccattaatta      60
catatgccca ttagtctaca aactgaaagt gcaatgaaga agacatatca aataagtaag     120
atgctaagat gcggaggaaa ctgcaacttg rgttgttctt tctttatcct ttgcctccct     180
aagttgcttc cacttctcaa tggaattagt tcccccgttt tgatcaggta tcttaccatc     240
atcaaggacc ttgtgacacc cggcttacca cctccttta ttttgaatac agcatcacat     300
t                                                                    301

<210> SEQ ID NO 21
<211> LENGTH: 240
<212> TYPE: DNA
<213> ORGANISM: Brassica napus

<400> SEQUENCE: 21
cgtaggtcgg agtagtatag taggtcctga ttaaatcgcc ttgcgtagaa cggatatgac      60
gaaggtagaa gtagaaaaaa caagtgttag ctcacttggc agcgaaagtt gcagagcgag     120
agagaacaag gttgagaaaa atggcgagca tgtctgcttt ccccgttttc cctctccgct     180
gcttctccgg taactckcat tttcgaatcg cagttctaat ctctcgaaga gtgcctgcag     240

<210> SEQ ID NO 22
<211> LENGTH: 121
<212> TYPE: DNA
<213> ORGANISM: Brassica napus

<400> SEQUENCE: 22
agatatcgat ttgttaagga attaaaagtt caatttattc tgrttataac ccmgtaaaga      60
racccattaa acgatgtcgt ttcctattca cgttaaatcg ccttgcgtag aacggrtatg     120
a                                                                    121

<210> SEQ ID NO 23
<211> LENGTH: 301
<212> TYPE: DNA
<213> ORGANISM: Brassica napus

<400> SEQUENCE: 23
agctcctgtt aaccaaattt catttaacat caacaccagt gtattcctcc taaccaaatc      60
tacaaatcat cctaaaaccc acccaaaaat aaataaaaat tcaataaaag caataataag     120
aaacttaaaa cacacatttt gttttaacaa wagtcttcaa gtgtactgtc catggagtta     180
tctctcctct gattttccga ccgaactgat ctatttccag tctgctcacc accagactcc     240
accgtagggg gaagcggaga aggcgaggca gactttttct gacgttttct ggagtgtctc     300
a                                                                    301
```

-continued

<210> SEQ ID NO 24
<211> LENGTH: 301
<212> TYPE: DNA
<213> ORGANISM: Brassica napus

<400> SEQUENCE: 24
cagtgtattc ctcctaacca aatctacaaa tcatcctaaa acccacccaa aaataaataa        60
aaattcaata aaagcaataa taagaaactt aaaacacaca ttttgttta acaatagtct        120 tcaagtgtac tgtccatgga gttatctctc ytctgatttt ccgaccgaac tgatctattt       180
ccagtctgct caccaccaga ctccaccgta gggggaagcg gagaaggcga ggcagacttt       240
ttctgacgtt ttctggagtg tctcacctta atgcacagag tcaaaacctg cacaacgtcc       300
c                                                                      301

<210> SEQ ID NO 25
<211> LENGTH: 301
<212> TYPE: DNA
<213> ORGANISM: Brassica napus

<400> SEQUENCE: 25
ataaaagcaa taataagaaa cttaaaacac acattttgtt ttaacaatag tcttcaagtg        60
tactgtccat ggagttatct ctcctctgat tttccgaccg aactgatcta tttccagtct       120
gctcaccacc agactccacc gtaggggaa kcggagaagg cgaggcagac tttttctgac        180
gttttctgga gtgtctcacc ttaatgacac gagtcaaaac ctgcacaacg tccctcatgt       240
agggacgttt cctcggtgca cgagagatgc atttataagc aaaagccgca acttcattca       300
c                                                                      301

<210> SEQ ID NO 26
<211> LENGTH: 301
<212> TYPE: DNA
<213> ORGANISM: Brassica napus

<400> SEQUENCE: 26
aagatataac atcataaatc cgtcaagatt gaatcaacta aacactgtaa aacaagatcc        60
atatatctcc ttagaagaaa agtctaatct ttatcagtca agagacagtt aaaccaagaa       120
tgcaagatgt atgatcatat cagtcaacat ytaacattaa aaacaaacca aacactctaa       180
aaacattata cattccaata atgtataatc ttttatcagc taagagacaa taaacaaaca       240
aaataagaca ttgcagagga aacacagaga caaacctgta agaatattcc aaaatgccag       300
a                                                                      301

<210> SEQ ID NO 27
<211> LENGTH: 301
<212> TYPE: DNA
<213> ORGANISM: Brassica napus

<400> SEQUENCE: 27
ataatctcac caactcatca tatgaaggta aattggagta atttaattgt gtcaaggatt        60
gatgacagaa aactatatta tccaaatatc cggtttatct tatgaatgca gttgagagtt       120
tggaggttaa taggtgagaa gataaaatgt saaactatat atacttccat atccagttgc       180
aagcagttac aatatgttca cctaaaactc acctaatctc atattcagga ttattagtta       240
tagttcattt tcatccaagg cgacataaat aatgacacca gttcaaaagg acaatatgat       300
g                                                                      301

-continued

```
<210> SEQ ID NO 28
<211> LENGTH: 301
<212> TYPE: DNA
<213> ORGANISM: Brassica napus

<400> SEQUENCE: 28
tcatcatatg aaggtaaatt ggagtaattt aattgtgtca aggattgatg acagaaaact      60
atattatcca aatatccggt ttatcttatg aatgcagttg agagtttgga ggttaatagg     120
tgagaagata aaatgtcaaa ctatatatac ytccatatcc agttgcaagc agttacaata     180
tgttcaccta aaactcacct aatctcatat tcaggattat tagttatagt tcattttcat     240
ccaaggcgac ataaataatg acaccagttc aaaaggacaa tatgatgttc ttgcttattt     300
c                                                                      301

<210> SEQ ID NO 29
<211> LENGTH: 301
<212> TYPE: DNA
<213> ORGANISM: Brassica napus

<400> SEQUENCE: 29
attgtgtcaa ggattgatga cagaaaacta tattatccaa atatccggtt tatcttatga      60
atgcagttga gagtttggag gttaataggt gagaagataa aatgtcaaac tatatatact     120
tccatatcca gttgcaagca gttacaatat rttcacctaa aactcaccta atctcatatt     180
caggattatt agttatagtt cattttcatc caaggcgaca taaataatga caccagttca     240
aaaggacaat atgatgttct tgcttatttc tccaccacca ttctaacaat tccttgatac     300
c                                                                      301

<210> SEQ ID NO 30
<211> LENGTH: 121
<212> TYPE: DNA
<213> ORGANISM: Brassica napus

<400> SEQUENCE: 30 ataaataag tttttaacaa acattagttt gatttcatgt taaacttta ggtttgatat        60 rgttcagctt tcccattaga ctactacggt aaaactaaga atttcttctt ttttytaaag     120
t                                                                      121

<210> SEQ ID NO 31
<211> LENGTH: 301
<212> TYPE: DNA
<213> ORGANISM: Brassica napus

<400> SEQUENCE: 31
ctaaatttta tatagaatca aatgccatag ggtagtgttt tctgctttgc ttgtaaaatg      60
aaaagtttca gtggaaaatt attttttactt aattatttac aggaaatgat ttggaacgaa     120
taaaatgttt gtattggtcc ctgagaaatt rttttcataa tgctagctac tctagttttg     180
taaagaaaaa tgtacctaat agaccacatg cactatcatt taacattgtc ttcactgtca     240
ctattttcct aataatwaat aacatacaaa gtaaggaaaa acagatttt tatttattta       300 g                                                                      301

<210> SEQ ID NO 32
<211> LENGTH: 1332
<212> TYPE: DNA
```

-continued

```
<213> ORGANISM: Brassica napus
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (400)..(400)
<223> OTHER INFORMATION: n is a, c, g, or t
<220> FEATURE:
<221> NAME/KEY: misc_feature
<222> LOCATION: (821)..(821)
<223> OTHER INFORMATION: n is a, c, g, or t
<220> FEATURE:
<221> NAME/KEY: misc_feature
<222> LOCATION: (1285)..(1285)
<223> OTHER INFORMATION: n is a, c, g, or t
<220> FEATURE:
<221> NAME/KEY: misc_feature
<222> LOCATION: (1286)..(1286)
<223> OTHER INFORMATION: n is a, c, g, or t
<220> FEATURE:
<221> NAME/KEY: misc_feature
<222> LOCATION: (1287)..(1287)
<223> OTHER INFORMATION: n is a, c, g, or t
<220> FEATURE:
<221> NAME/KEY: misc_feature
<222> LOCATION: (1288)..(1288)
<223> OTHER INFORMATION: n is a, c, g, or t
<220> FEATURE:
<221> NAME/KEY: misc_feature
<222> LOCATION: (1289)..(1289)
<223> OTHER INFORMATION: n is a, c, g, or t
<220> FEATURE:
<221> NAME/KEY: misc_feature
```

-continued

```
<222> LOCATION: (1290)..(1290)
<223> OTHER INFORMATION: n is a, c, g, or t
<220> FEATURE:
<221> NAME/KEY: misc_feature
<222> LOCATION: (1291)..(1291)
<223> OTHER INFORMATION: n is a, c, g, or t
<220> FEATURE:
<221> NAME/KEY: misc_feature
<222> LOCATION: (1292)..(1292)
<223> OTHER INFORMATION: n is a, c, g, or t
<220> FEATURE:
<221> NAME/KEY: misc_feature
<222> LOCATION: (1293)..(1293)
<223> OTHER INFORMATION: n is a, c, g, or t
<220> FEATURE:
<221> NAME/KEY: misc_feature
<222> LOCATION: (1294)..(1294)
<223> OTHER INFORMATION: n is a, c, g, or t
<220> FEATURE:
<221> NAME/KEY: misc_feature
<222> LOCATION: (1295)..(1295)
<223> OTHER INFORMATION: n is a, c, g, or t
<220> FEATURE:
<221> NAME/KEY: misc_feature
<222> LOCATION: (1296)..(1296)
<223> OTHER INFORMATION: n is a, c, g, or t
<220> FEATURE:
<221> NAME/KEY: misc_feature
<222> LOCATION: (1297)..(1297)
<223> OTHER INFORMATION: n is a, c, g, or t
<220> FEATURE:
<221> NAME/KEY: misc_feature
<222> LOCATION: (1298)..(1298)
<223> OTHER INFORMATION: n is a, c, g, or t
<220> FEATURE:
<221> NAME/KEY: misc_feature
<222> LOCATION: (1299)..(1299)
<223> OTHER INFORMATION: n is a, c, g, or t
<220> FEATURE:
<221> NAME/KEY: misc_feature
<222> LOCATION: (1300)..(1300)
<223> OTHER INFORMATION: n is a, c, g, or t
<220> FEATURE:
<221> NAME/KEY: misc_feature
<222> LOCATION: (1301)..(1301)
<223> OTHER INFORMATION: n is a, c, g, or t
<220> FEATURE:
<221> NAME/KEY: misc_feature
<222> LOCATION: (1302)..(1302)
<223> OTHER INFORMATION: n is a, c, g, or t
<220> FEATURE:
<221> NAME/KEY: misc_feature
<222> LOCATION: (1303)..(1303)
<223> OTHER INFORMATION: n is a, c, g, or t
<220> FEATURE:
<221> NAME/KEY: misc_feature
<222> LOCATION: (1304)..(1304)
<223> OTHER INFORMATION: n is a, c, g, or t
<220> FEATURE:
<221> NAME/KEY: misc_feature
<222> LOCATION: (1305)..(1305)
<223> OTHER INFORMATION: n is a, c, g, or t
<220> FEATURE:
<221> NAME/KEY: misc_feature
<222> LOCATION: (1306)..(1306)
<223> OTHER INFORMATION: n is a, c, g, or t
<220> FEATURE:
<221> NAME/KEY: misc_feature
<222> LOCATION: (1307)..(1307)
<223> OTHER INFORMATION: n is a, c, g, or t
<220> FEATURE:
<221> NAME/KEY: misc_feature
<222> LOCATION: (1308)..(1308)
<223> OTHER INFORMATION: n is a, c, g, or t
<220> FEATURE:
<221> NAME/KEY: misc_feature
<222> LOCATION: (1309)..(1309)
<223> OTHER INFORMATION: n is a, c, g, or t
<220> FEATURE:
```

-continued

```
<221> NAME/KEY: misc_feature
<222> LOCATION: (1310)..(1310)
<223> OTHER INFORMATION: n is a, c, g, or t
<220> FEATURE:
<221> NAME/KEY: misc_feature
<222> LOCATION: (1311)..(1311)
<223> OTHER INFORMATION: n is a, c, g, or t
<220> FEATURE:
<221> NAME/KEY: misc_feature
<222> LOCATION: (1312)..(1312)
<223> OTHER INFORMATION: n is a, c, g, or t
<220> FEATURE:
<221> NAME/KEY: misc_feature
<222> LOCATION: (1313)..(1313)
<223> OTHER INFORMATION: n is a, c, g, or t
<220> FEATURE:
<221> NAME/KEY: misc_feature
<222> LOCATION: (1314)..(1314)
<223> OTHER INFORMATION: n is a, c, g, or t
<220> FEATURE:
<221> NAME/KEY: misc_feature
<222> LOCATION: (1315)..(1315)
<223> OTHER INFORMATION: n is a, c, g, or t
<220> FEATURE:
<221> NAME/KEY: misc_feature
<222> LOCATION: (1316)..(1316)
<223> OTHER INFORMATION: n is a, c, g, or t
<220> FEATURE:
<221> NAME/KEY: misc_feature
<222> LOCATION: (1317)..(1317)
<223> OTHER INFORMATION: n is a, c, g, or t
<220> FEATURE:
<221> NAME/KEY: misc_feature
<222> LOCATION: (1318)..(1318)
<223> OTHER INFORMATION: n is a, c, g, or t
<220> FEATURE:
<221> NAME/KEY: misc_feature
<222> LOCATION: (1319)..(1319)
<223> OTHER INFORMATION: n is a, c, g, or t
<220> FEATURE:
<221> NAME/KEY: misc_feature
<222> LOCATION: (1320)..(1320)
<223> OTHER INFORMATION: n is a, c, g, or t
<220> FEATURE:
<221> NAME/KEY: misc_feature
<222> LOCATION: (1321)..(1321)
<223> OTHER INFORMATION: n is a, c, g, or t
<220> FEATURE:
<221> NAME/KEY: misc_feature
<222> LOCATION: (1322)..(1322)
<223> OTHER INFORMATION: n is a, c, g, or t
<220> FEATURE:
<221> NAME/KEY: misc_feature
<222> LOCATION: (1323)..(1323)
<223> OTHER INFORMATION: n is a, c, g, or t
<220> FEATURE:
<221> NAME/KEY: misc_feature
<222> LOCATION: (1324)..(1324)
<223> OTHER INFORMATION: n is a, c, g, or t
<220> FEATURE:
<221> NAME/KEY: misc_feature
<222> LOCATION: (1325)..(1325)
<223> OTHER INFORMATION: n is a, c, g, or t
<220> FEATURE:
<221> NAME/KEY: misc_feature
<222> LOCATION: (1326)..(1326)
<223> OTHER INFORMATION: n is a, c, g, or t
<220> FEATURE:
<221> NAME/KEY: misc_feature
<222> LOCATION: (1327)..(1327)
<223> OTHER INFORMATION: n is a, c, g, or t
<220> FEATURE:
<221> NAME/KEY: misc_feature
<222> LOCATION: (1328)..(1328)
<223> OTHER INFORMATION: n is a, c, g, or t
<220> FEATURE:
<221> NAME/KEY: misc_feature
<222> LOCATION: (1329)..(1329)
<223> OTHER INFORMATION: n is a, c, g, or t
```

```
<220> FEATURE:
<221> NAME/KEY: misc_feature
<222> LOCATION: (1330)..(1330)
<223> OTHER INFORMATION: n is a, c, g, or t
<220> FEATURE:
<221> NAME/KEY: misc_feature
<222> LOCATION: (1331)..(1331)
<223> OTHER INFORMATION: n is a, c, g, or t
<220> FEATURE:
<221> NAME/KEY: misc_feature
<222> LOCATION: (1332)..(1332)
<223> OTHER INFORMATION: n is a, c, g, or t

<400> SEQUENCE: 32
nnnnnnnnnn ncagagaaac aaaagaanaa agaaacattc caagaatatc ttagagattt      60
caagaaaaat gggatcaacg gcggagacac agataactcc ggtacaagtc accgacgacg     120
aagccgctct ctttgccatg cagctagcca gcgcctccgt ccttcccatg gttttaaagt     180
ccgcgctaga ccttgatctt ctcgagatca tggccaagaa ctcttctccg atgtctccct     240
ctgagattgc ttctaaactt cagaccaaaa accccgaagc tccggtcatg ctcgaccgaa     300
tcctccgtct tctcacgtct tactccatcc tcacctgctc caaccgaacc attcccggcg     360
gagacagcgt cgagaggaty tacgggcttg gtccggtttn gcaagtactt gaccaagaac     420
gaagatggtg tctctatagc tgctctttgt cttatgaacc aagacaaggt tctcatggaa     480
agctggtacc atttgaaaga tgcaattctt gatggtggga ttccattcaa caaggcttat     540
ggaatgagcg cttttgagta ccacgggaag gatctaaggt tcaacacggt attcaacaat     600
ggaatgtcta accattcaac cattacaatg aagaagattc tcgagaccta taagggtttt     660
gagggtttga cttctttggt tgacgttggt ggtggcattg gtgctactct caaaatgatt     720
gtctctaagt accctgacct taaaggcatc aactttgatc tcccacatgt catcgaagaa     780
gctacttctc atcccggtat tgatcatgtt ggaggagata ntgtttgtaa gtgtccctaa     840
aggtgatgca attttcatga agtggatatg ccacgactgg agcgatgaac actgcgtgaa     900
attcttgaag aactgctacg aggcgcttcc agaggatgga aaagtgatac tagcagagtg     960
tatacttcca gagacaccag actcaagcct ctcgaccaaa caagtagtcc atgttgattg    1020
cattatgttg gctcacaacc ctggaggcaa agaacggacc gagaaggagt tcgaggcatt    1080
agctaaagga tcaggcttca aaggcatcaa tgttgcctgc aatgcttttg gtgtttacgt    1140
tattgagctg ctcaaaaaga tgtaagacac acacacacac acacaatcca tgtaataatg    1200
atattatatg taaacattgc tttcatgtac gtctacttca ccgtctttgt tttaaaacta    1260
tgatgtgtaa taatggttta ttaannnnnn nnnnnnnnnn nnnnnnnnnn nnnnnnnnnn    1320
nnnnnnnnnn nn                                                        1332

<210> SEQ ID NO 33
<211> LENGTH: 121
<212> TYPE: DNA
<213> ORGANISM: Brassica napus

<400> SEQUENCE: 33
tgtagatgtt tataatatta tatgtgaacg ttatatgatc gggtactttt ttctttgaaa      60
yttatatgat cggatactct taacgtaagt acgcatatga ttagcggatc actcacggca     120
g                                                                     121

<210> SEQ ID NO 34
<211> LENGTH: 301
<212> TYPE: DNA
```

<213> ORGANISM: Brassica napus

<400> SEQUENCE: 34

```
atatcgaact ctagaatttt caattcataa aatgaatttt taaatattcg gttatamygt        60
aaattcataa agcataaaat aaatattcat aatatattaa cattttctt acttatacac        120 gatttagttt tggtcattga ctatcaaata yattatgcaa gctattgttt tccattttat        180
tttccatttt atgcgagcta ttgtttttcca tttttttcatc atctattaat acttttttctt      240 tctttaacaa gatttagttt cattccatgt gtcaaacgaa tcatcaagtg cctgytatga        300
a                                                                         301
```

<210> SEQ ID NO 35
<211> LENGTH: 298
<212> TYPE: DNA
<213> ORGANISM: Brassica napus

<400> SEQUENCE: 35

```
aagtcttcca tggtagacct tttccctctg aaactacagt acccacagct cawgcttcca        60
tcatcactgt catcacacat aacccttatt aagtactact aaaaaaaaca aatataaaac        120
attggtccaa agccacattg cctacacaac agtaacgtat atcggaaaat cagtttcttc        180
agtacatgta attaattcaa taaccctaca agctattttc tacaacagag acaaatgaac        240
tcactttttc cagccaccac caatgtaccc gccgtcatca actttctcct tcgggata         298
```

<210> SEQ ID NO 36
<211> LENGTH: 121
<212> TYPE: DNA
<213> ORGANISM: Brassica napus

<400> SEQUENCE: 36

```
actagccaaa attgattgtt gggctttttgt aagaaacaca ctttattaat tagatataca       60
ygactattaa ctaccatctt tgacctcaaa acctattarc tacaatcttt gacctagaaa        120
c                                                                         121
```

<210> SEQ ID NO 37
<211> LENGTH: 121
<212> TYPE: DNA
<213> ORGANISM: Brassica napus

<400> SEQUENCE: 37

```
gcagtattct tttattgaag agaawattat agttawagtc tcatccatgt caatgtgact        60
yatcaggtat aatatctatg agaaggatga tcaagcatat aacaaaacta gataaccagt        120 m                                                                         121
```

<210> SEQ ID NO 38
<211> LENGTH: 121
<212> TYPE: DNA
<213> ORGANISM: Brassica napus

<400> SEQUENCE: 38

```
ccatatatat kcatgtatgt aagcatttac aacactaact aatgcattgt gtatataaat        60
kggtccctaa attttaacta aaacctaggg agtctaagag catcattatc crgmrtttct        120
t                                                                         121
```

<210> SEQ ID NO 39
<211> LENGTH: 121

```
<212> TYPE: DNA
<213> ORGANISM: Brassica napus

<400> SEQUENCE: 39
gatatgttga  dacgccagtc  cacatatgca  gtaccgaatg  taccwagagt  tgataaaaaa     60
rggtaatggt  tttctgtgcc  tcaaagcaac  acagtttagc  ttagcaatgc  aaggctgact    120
a                                                                        121

<210> SEQ ID NO 40
<211> LENGTH: 121
<212> TYPE: DNA
<213> ORGANISM: Brassica napus

<400> SEQUENCE: 40
tctttgtatg  atatgcaacc  tcgwtgcaac  attttgctcc  aaaagctcat  gtttatttct     60
ycatttacct  gttgtgacct  caataaatac  taaaagattc  gatacaacat  gaaaagttar    120 m                                                                        121

<210> SEQ ID NO 41
<211> LENGTH: 301
<212> TYPE: DNA
<213> ORGANISM: Brassica napus

<400> SEQUENCE: 41
agcattctat  tctctaaaag  cggttatgtt  caatcgtttt  aaaactttt  ttttctgaac     60 atgtaataaa  taattgaaga  tctttatttg  tattttatgt  ctggtttagg  tactaatctt    120
tacgcctata  tgcattctac  gttctttaat  ytaaaagctt  attgaatagg  ttgtaaaaaa    180
caagaattgt  atacgtgact  ttgtctatgt  aaacttggta  ttcaaaactg  gttgaccaaa    240
ccgtttgata  aatatatgga  tatttgctga  caagaaaaaa  gaccaaggac  cataattaac    300
a                                                                        301

<210> SEQ ID NO 42
<211> LENGTH: 301
<212> TYPE: DNA
<213> ORGANISM: Brassica napus

<400> SEQUENCE: 42
atccaaatgt  tacaaccaaa  atacagtgaa  aaacacaaag  catttacata  tttaattgaa     60
tttgatcgat  atatctcttt  caaataaacc  acataggtct  cactgccaat  aacatccgga    120
atcctttaaa  caccgcaatt  tttctctcta  ragtctctcc  cctcagcttc  acaaacccct    180
aaatcagccg  tcgcatcttt  ttcctctggt  gaccggtagc  tctcttgctc  cggtcgccac    240
cccagtccgt  catgcgttct  agccttcttc  cttagcctct  ttgtcctacc  cttctccttc    300
t                                                                        301

<210> SEQ ID NO 43
<211> LENGTH: 301
<212> TYPE: DNA
<213> ORGANISM: Brassica napus

<400> SEQUENCE: 43
ttgttgaacc  ccaccaatta  atatttatca  tactcttcgc  cattttgat  gtttcgggtc     60 atttcacatt  tgcttatttc  gtatattata  aaagaaagca  aaactgtaaa  caaacttggg    120
aacaaaattc  aaactgatat  tgttttgttt  waaaaaacat  ttctattaat  ttgcttgatt    180
```

-continued

```
cttataatag tggtgacatt tagaaccata ataatttgtt cgaacactgt ataactatat          240
atacttacaa aggaccacaa aaatatcttt ctcttcaatt taaaccattc catagtggag          300
a                                                                           301

<210> SEQ ID NO 44
<211> LENGTH: 301
<212> TYPE: DNA
<213> ORGANISM: Brassica napus

<400> SEQUENCE: 44
cgggtcattt cacatttgct tatttcgtat attataaaag aaagcaaaac tgtaaacaaa           60
cttgggaaca aaattcaaac tgatattgtt ttgtttaaaa aaacatttct attaatttgc          120
ttgattctta taatagtggt gacatttaga wccataataa tttgttcgaa cactgtataa          180
ctatatatac ttacaaagga ccacaaaaat atctttctct tcaatttaaa ccattccata          240
gtggagacaa attcaaaatc aatatatccg taacatcatg cacctaggaa ctgttatccc          300
g                                                                           301

<210> SEQ ID NO 45
<211> LENGTH: 301
<212> TYPE: DNA
<213> ORGANISM: Brassica napus

<400> SEQUENCE: 45
cactagcagt ttgatattgt cattctggga catccatttt aatcggagca tttacagctg           60
gtacttgtga cttaatcact ttcttatggt cagtaaatga gtctggtaac tcatatgcta          120
atctttgtaa tagaattatc tccatacatt yattttggac ttccatttac gctctttagt          180
ccgaggatca atgataattc attttaactc attcattctc caacgtaact gtttattttc          240
tccctctatt gttggataga ctaactttga gtctttacat aaatcttata aaagcttcta          300
g                                                                           301

<210> SEQ ID NO 46
<211> LENGTH: 301
<212> TYPE: DNA
<213> ORGANISM: Brassica napus

<400> SEQUENCE: 46
atacccgaaa ccgcacagaa atcactcact cacccatctt cttcatggtg attcttacat           60
agatgagaaa tgattagcac aagacgtttg ttggttgttt aatattcatg cgggatattg          120
tctccttctt cactatttgg taaagctaga rgaaactgtg aaacaaatat actatggtta          180
aattatatat atgatggggc tgattatttg aattggttga gcaggagatt tttttctttg          240
tcaactagca ggggatttac ttatataatt tgtattgtga tgcttgattt acgtgatttc          300
t                                                                           301

<210> SEQ ID NO 47
<211> LENGTH: 121
<212> TYPE: DNA
<213> ORGANISM: Brassica napus

<400> SEQUENCE: 47
ttagtagcag caagatgcgt ttgtgtatct ttcttgtttc taatgcgact gaattgtatt           60
rtatgctggt aaatggtaac tgtgtgtctg tgttaaagaa atatgcaagg acgctagtct          120
t                                                                           121
```

-continued

```
<210> SEQ ID NO 48
<211> LENGTH: 301
<212> TYPE: DNA
<213> ORGANISM: Brassica napus

<400> SEQUENCE: 48
ttatgtcatt gtgaaagtgt agtttatgaa tgtggtaaac atatttacat aaatatctgc      60
ctgcctggtc ttttttgctt gtagttaatg tatgtagcaa acttactctg tcttcttagt     120
ctagattgat attctgaaaa ttaaatttct ractccaaaa tgttaaactg caatttaatt     180
gaagattgca tatatcaaag gtttaaatgg taggatcacc cgcttgcttt cagtgaactg     240
ggttccaagt tatgtattga acaatactag gatcttcacc ccgcgcaagc gcggggatag     300
a                                                                     301

<210> SEQ ID NO 49
<211> LENGTH: 301
<212> TYPE: DNA
<213> ORGANISM: Brassica napus

<400> SEQUENCE: 49
agtttatgaa tgtggtaaac atatttacat aaatatctgc ctgcctggtc ttttttgctt      60
gtagttaatg tatgtagcaa acttactctg tcttcttagt ctagattgat attctgaaaa     120
ttaaatttct gactccaaaa tgttaaactg saatttaatt gaagattgca tatatcaaag     180
gtttaaatgg taggatcacc cgcttgcttt cagtgaactg ggttccaagt tatgtattga     240
acaatactag gatcttcacc ccgcgcaagc gcggggatag aaggagttcg atttctatgt     300
a                                                                     301

<210> SEQ ID NO 50
<211> LENGTH: 301
<212> TYPE: DNA
<213> ORGANISM: Brassica napus

<400> SEQUENCE: 50
tagattgata ttctgaaaat taaatttctg actccaaaat gttaaactgc aatttaattg      60
aagattgcat atatcaaagg tttaaatggt aggatcaccc gcttgctttc agtgaactgg     120
gttccaagtt atgtattgaa caatactagg rtcttcaccc cgcgcaagcg cggggataga     180
aggagttcga tttctatgta gtaaacaatt gtgcgggcta tatatatttt gtgtcttatt     240
gttttatggt cccatttcat atttatttgc atatttggtt tcataccaca attatctctt     300
g                                                                     301

<210> SEQ ID NO 51
<211> LENGTH: 301
<212> TYPE: DNA
<213> ORGANISM: Brassica napus

<400> SEQUENCE: 51
ttctgaaaat taaatttctg actccaaaat gttaaactgc aatttaattg aagattgcat      60
atatcaaagg tttaaatggt aggatcaccc gcttgctttc agtgaactgg gttccaagtt     120
atgtattgaa caatactagg atcttcaccc ygcgcaagcg cggggataga aggagttcga     180
tttctatgta gtaaacaatt gtgcgggcta tatatatttt gtgtcttatt gttttatggt     240
cccatttcat atttatttgc atatttggtt tcataccaca attatctctt gaattgtcat     300
```

-continued

```
t                                                                        301

<210> SEQ ID NO 52
<211> LENGTH: 121
<212> TYPE: DNA
<213> ORGANISM: Brassica napus

<400> SEQUENCE: 52
aaatcagaac ggaggccgaa gtataagcaa gaaatatgga cgatagtttg aacaaaaaga        60
rcaataaatt atactgaart gttaagtgtt catgacattt gatcatagtt atatgttcat       120
g                                                                       121

<210> SEQ ID NO 53
<211> LENGTH: 121
<212> TYPE: DNA
<213> ORGANISM: Brassica napus

<400> SEQUENCE: 53
atcactacgg ttcaactttg gcatgctagt gaaccgtagt gatgctagtg atattcccac        60
ygggtcaatt aaccacaaag tgktcatgaa tttctgttct aaggagtttt ggatgcaata       120
c                                                                       121

<210> SEQ ID NO 54
<211> LENGTH: 934
<212> TYPE: DNA
<213> ORGANISM: Brassica napus

<400> SEQUENCE: 54
aactataaca acgaaaacat aatacatgtt ttggctataa ttgtttgagg gcacccacga        60
actcatatcc taaggtagca aaaagatcgc atcctctagc tcgtggacgg ggtaatcgcg       120
gtggaggtaa agaggtggac gtggataatt tcgtctttga cgttatgaac tctccaagta       180
cttgagtttg agaactctcg gtccttactc tatcccttct tctctattag gaacttgtat       240
tacttctaaa catcagctaa ttagctctcg cttatctcta cttttaaaaa ctgcatgact       300
ttgtcatagc tgtaatggtt acttgcaagt aaatagaaag ttttttttttt taaaaaagaa       360 gaagataaac gaagaacatg gttacatgga agttaattaa taagaatgac aaatacatat       420
ttacttagaa aatkaagaag agttcggctc cctgacgttc ttacctttttt gttaaaagat       480 aagttcgtgt tctttccatg acaaaagtat atttggtcca ttacatagtt caattttcct       540
tttgtctcta ctatgaaaga ataagttgtt tattgtgtat gtgtttatac atttagacca       600 aaggtttttaa cctcaaaagc tttgacttca aaagctgttt cttttgtgaa tttcaaaaat       660
ttcgaccttc tttcacttta aagtctaaag aacggtgtgc acaaaaaaaa aggggtctaa       720
agaacggttt gctttgtaac ttttttttgtt caacacattt tcttttaact ttaatacaaa       780
tgagaatcaa aatattattt ttaataagtt attgattagc ctaacaatgt tttatacttt       840
tcagctttgt ttttaaatgt ttttgggttc aattttaaga tcccattctt gttctagtat       900
tcttgttttc actgcagcaa cgtatgatta tgaa                                   934

<210> SEQ ID NO 55
<211> LENGTH: 301
<212> TYPE: DNA
<213> ORGANISM: Brassica napus

<400> SEQUENCE: 55
tcataaaaac ggcgagcact gcgacgtcac agctcaaacc cgacacgatg ttcttcgatg        60
```

```
actctgtttc ctctgtttct tcatcaaaga gattctttga cctcataaag cctctataca        120
acaaaacaac caagaaacag agcgtcaaca stgtatccac atctcctgcg tctttaccgg        180
cgacggcgag ggagaaacag aggaataata aaccgtcagg gattcgaaga cagcttggga        240
agagccggtc ggcgtctgcg actttgtctc cggcgaagag agtcgacgag tctttacagg        300
t                                                                        301
```

```
<210> SEQ ID NO 56
<211> LENGTH: 121
<212> TYPE: DNA
<213> ORGANISM: Brassica napus

<400> SEQUENCE: 56
tctrcaagaa aagccctttc tsaaaaaaga aaaaattcya ccaagaaata tttttrgctc         60
mttactgtga agattaatta tggcatattg tgagatgtgt gacagacgaa gacgacagag        120
t                                                                        121
```

```
<210> SEQ ID NO 57
<211> LENGTH: 121
<212> TYPE: DNA
<213> ORGANISM: Brassica napus

<400> SEQUENCE: 57
aggagyaaaa atatgaatga attaagagct ggtgttttat tcgaaattta atatttaggt         60
kacgaaataa attcgaactt cgactttacy gtacagatta atggattgtg tgaatggtga        120
c                                                                        121
```

```
<210> SEQ ID NO 58
<211> LENGTH: 121
<212> TYPE: DNA
<213> ORGANISM: Brassica napus

<400> SEQUENCE: 58
tacttaaaca ataacttaaa aatatgtagt atatgtcaca tagtcactcg tttaggtcgt         60
ytgttagcgc atgtaatcaa cccaaatata ctattctagt caacaaagga atgaattcca        120
c                                                                        121
```

```
<210> SEQ ID NO 59
<211> LENGTH: 301
<212> TYPE: DNA
<213> ORGANISM: Brassica napus

<400> SEQUENCE: 59
tggacgtctg tggtatcagg gtttgtacga aacttgagag ccaaggaagc agttgctaaa         60
tttcatgaga tgctaggttt gggtttgcaa cccaataact ttacatactt tgcaatcttg        120
atcttgtgtt cctctgtcca gttggtggat waggcaaga agattcgttc acaggcaata        180
aaggtcgctt ggaggacagc attgatatcg aaaattcact tgtagatatt tagatgaagt        240
gctaggcatc ataaattgtc tgtctcttag acaacgttaa tcttaggtca agcggattac        300
g                                                                        301
```

```
<210> SEQ ID NO 60
<211> LENGTH: 201
<212> TYPE: DNA
<213> ORGANISM: Brassica napus
```

-continued

```
<400> SEQUENCE: 60
cttatcacat tcttgtgttg tactatgcta ccgagtctgc ccttttcaac cttttttgttc      60 tgagtttgct cattttacaa acactttcat caccgtggag ytgtaatgtc ttttgatttg     120
cgattgcaga atgggaccct tggggtgttc cagatgacta cgagtgtgaa gtaattgaga     180
acgatgcacc cattcccaag c                                               201

<210> SEQ ID NO 61
<211> LENGTH: 494
<212> TYPE: DNA
<213> ORGANISM: Brassica napus
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (468)..(468)
<223> OTHER INFORMATION: n is a, c, g, or t
<220> FEATURE:
<221> NAME/KEY: misc_feature
<222> LOCATION: (479)..(479)
<223> OTHER INFORMATION: n is a, c, g, or t

<400> SEQUENCE: 61
aatgtgtgca aggaagagga agactgggag gcgatcgaga agcgtcttgg ctgcggtcaa      60
gtcgaggagc tcatcgagga ggcgcaagat gagctcacac tcattgcgaa gatgatcgaa     120 tgggacccctt ggggtgttcc agatgactac gagtgtgaag taattgagaa cgatgcaccc     180
attcccaagc acgttcctca gcatcgacct ggtcctcttc ctgaggattt ctacagaacc     240
cttgaaggtc taattacaga gtccaaaaca aaaatcccag ctgccgctac ctccactgat     300
ycgcagttga aggagtgagt aacttccagt tctacattgt ttgtttgtgt tctttgttgc     360
tttgtttggc cactgttcag agacagcgag cctatgaata aactggttaa taatctttga     420
aaactagaac anatatcact cgtttcataa atgtttttat ctttcttnct caaagaacng     480
tatgataata caaa                                                       494

<210> SEQ ID NO 62
<211> LENGTH: 448
<212> TYPE: DNA
<213> ORGANISM: Brassica napus

<400> SEQUENCE: 62
aattcgttca aacttttctg gtagtttgga ttgtttttaag gtcttacttt tcctatttgg      60
ccgactctgc atgtccagtt tttgtcatta tactatcaag tgaacattac cctggctaag     120
taactaatta acaattctgg tttctgcaac tagagtgttc tttagttttt gcagctttac     180
tacactcttc attttactac tttcttactt atcaaagtat atgataccaa cagcaagtgt     240
gaagaaaaat gatgacactg aaggttgtca gactaagtat aaaccaaaac ccaattctac     300
ttgactagac aaaaatataa tttgcccaaa aacaaactat ttgaacaaga gagataaagat     360 ggaagggaaw cattaattta agaacggatg tttgctccaa caacgaaact taactcagat     420
aaaaaaaaca tgaagatagt ccagaatt                                        448

<210> SEQ ID NO 63
<211> LENGTH: 301
<212> TYPE: DNA
<213> ORGANISM: Brassica napus

<400> SEQUENCE: 63
```

-continued

```
cccgagttga gaactagagt aaggcagtac aaatggtcaa aatcttggcg attcaagttc        60
aaggacaagt caatggaaca cacattatca actggtctct ggtttgtacg gtgataatca       120
gatgcttcta gatgatatag ttsaggaagg ytcagtccta gtggagaagt ttgcctcagt       180
agagatatat aacaaagctc gtttactgct gaagttgatt catatggagt tcattggagg       240
caaagcccgt gacaatgggc tgttagttgc aggtcaaatc aagatttatg tgtgaattct       300
c                                                                       301
```

<210> SEQ ID NO 64
<211> LENGTH: 301
<212> TYPE: DNA
<213> ORGANISM: Brassica napus

<400> SEQUENCE: 64

```
aatcaaatgg tggaagacag tgttgatgat caaaaggtgg ttaaaacaat ggttcaagat        60
attaccgacc aagataaacc tactgaagtt aatgctgtta ctgctagcta ctttgttgac       120
gctgaattgc agttgacaag gaaaagcata kagtagcttc tctaatggtg ttgagatgcc       180
tcaggacttg tttgttatca tgaagctgga ttgtgcagat ccatttcgtt gacactacgt       240
ctccccatga agaattgttg agaactagag taaggcagta caaatggtca aaatcttggc       300
g                                                                       301
```

<210> SEQ ID NO 65
<211> LENGTH: 301
<212> TYPE: DNA
<213> ORGANISM: Brassica napus

<400> SEQUENCE: 65

```
ctctgtagcc gtaaacttcc ctttatctgc cttaagcaac attccgagaa gatcacggtg        60
gtcgtctcca tcgaccaaag atctctttcg ttcgtttatg atcgacaaaa ggagaccatc       120
gatctctttg cctaactctc tagctttgag rgtttgcttg taggccaaaa tgttgctaaa       180
aggtacccct acgtagcgat ttgagttgaa gagagcgaat tgcacggctc ttaggttttt       240
gaggacttga gctccgtttt ctcccttgac tccgaagctt gtcttagcaa tgatctcacc       300
g                                                                       301
```

<210> SEQ ID NO 66
<211> LENGTH: 301
<212> TYPE: DNA
<213> ORGANISM: Brassica napus

<400> SEQUENCE: 66

```
tgtcattata gaatgcaatg atgatggtgt tataatgact taaacaggtt acaatcctcg        60
gaatggctat caagtacggt gggaagtatg tggactcatt tctaaaaggt ataatctctt       120
ccataatttc acacaagagt tgaattacct racgttttgt tggcttattt gagatttgaa       180
acaacaaatg tgcagttttt ttattttcct ggaagcacat tttcaagatc ataatgaatt       240
agtcttccag ctggtaaatt tggtgttctt tgccttttcc tttactgatc tctctgtcca       300
c                                                                       301
```

<210> SEQ ID NO 67
<211> LENGTH: 201
<212> TYPE: DNA
<213> ORGANISM: Brassica napus -continued

```
<400> SEQUENCE: 67
cattcagtaa cgataaagcc attgagattt tgaagagaga ttagtgtgca gtcatgtcgt      60
acccrkccag aagttggagc ckcgtgagtt gtacggagaa kagccttcac gttaaacaga     120
aagcgctctg gagatctctt tgttgctggt attttgctgg tgatggctga ttgwttcmtm     180
ccttaaaaaa aaactcatat a                                               201

<210> SEQ ID NO 68
<211> LENGTH: 301
<212> TYPE: DNA
<213> ORGANISM: Brassica napus

<400> SEQUENCE: 68
tctctcttca aaatctcaat ggctttatcg ttactgaatg ctgcgaacca tttacgtaga      60
ttctcctcta aaattttcac ttccgaaaac ttgaaatcta aatagatccg aaccaaactc     120
gaaaagatat tcaaacgccc acccctgctt mactccaaca acaacaaaac acaccaatgt     180
caaatagcag ataaactagc actgagtgaa tgctcgtata caacctaatg ccgtagaccg     240
tttatataga ttcgagttta cagttataca acaaaatagt atttattttg gttgcaagaa     300
a                                                                     301

<210> SEQ ID NO 69
<211> LENGTH: 301
<212> TYPE: DNA
<213> ORGANISM: Brassica napus

<400> SEQUENCE: 69
gggacgatct tgaggacgat ttctatgaag agcctaaaag cagcaagaag atgaagaggt      60
ctgatgctac tgcacctaat gatttagatc agaagagcat ccctgaaaag aaacaaggtc     120
caaaggttgt caatttcttt ggatgataca rgaggatcta aaaggtctat caattttgta     180
gggaaatatc agtttttgt tgttctttat ctgcctctag agtttgtgta aggactattt     240
gctatttgga gtttcacaac agtgtcatgt aatggaaccg gtgaaccaca gtcacttctg     300
t                                                                     301

<210> SEQ ID NO 70
<211> LENGTH: 301
<212> TYPE: DNA
<213> ORGANISM: Brassica napus

<400> SEQUENCE: 70
aggacgattt ctatgaagag cctaaaagca gcaagaagat gaagaggtct gatgctactg      60
cacctaatga tttagatcag aagagcatcc ctgaaaagaa acaaggtcca aaggttgtca     120
atttctttgg atgatacagg aggatctaaa rggtctatca attttgtagg gaaatatcag     180 tttttttgttg ttctttatct gcctctagag tttgtgtaag gactatttgc tatttggagt     240
ttcacaacag tgtcatgtaa tggaaccggt gaaccacagt cacttctgtt tcagataatc     300
t                                                                     301

<210> SEQ ID NO 71
<211> LENGTH: 301
<212> TYPE: DNA
<213> ORGANISM: Brassica napus

<400> SEQUENCE: 71
cacccaccat ctcaatgtcc attctggttc gaaaaggaaa cagtacatta ctgggaaaga      60
```

-continued

```
tgagacttat atggaagact cggtccattg tgttccctcg acagagtttg ctggttcgaa      120
gcgcaagcct tcaggggatt tccaacttga kgatccttgg tcatctagag atcatgagat      180
gtttcatttt gaccctgtca ctgagttccc cgatgcacct ctcaaacctt ctgggatcat      240
tcatcctaat gactcttggc catctaaaga tcctgagagg tttgacaaca agtcaggacc      300
t                                                                      301

<210> SEQ ID NO 72
<211> LENGTH: 301
<212> TYPE: DNA
<213> ORGANISM: Brassica napus

<400> SEQUENCE: 72
atatggaaga ctcggtccat tgtgttccct cgacagagtt tgctggttcg aagcgcaagc       60
cttcagggga tttccaactt gaggatcctt ggtcatctag agatcatgag atgtttcatt      120
ttgaccctgt cactgagttc cccgatgcac stctcaaacc ttctgggatc attcatccta      180
atgactcttg gccatctaaa gatcctgaga ggtttgacaa caagtcagga cctggttctt      240
catcaaagga cacgttctgg gagactgatt ttggagtcga ggataacctt cctggatttg      300
a                                                                      301

<210> SEQ ID NO 73
<211> LENGTH: 301
<212> TYPE: DNA
<213> ORGANISM: Brassica napus

<400> SEQUENCE: 73
ctctgtttcc gtacctgctg cttttgattc gtctctcatc ttggtgagct tcggaaacct       60
caccttcaag catctgttct ggactttcat cgacaaatct ttgtgcttct cttccacgtt      120
ttttttgtct ctctctctgt tacgtaatct mactctctgc tatctcttgc atttcctcta      180 gattttgtt ctgcagacga aggttgtttg cttcagccaa tttctttgtt gtcaggttct      240
catgctcgtg atcgatcctc gatctctttc tttaaactcc ttaacctgac tctccagttc      300
a                                                                      301

<210> SEQ ID NO 74
<211> LENGTH: 301
<212> TYPE: DNA
<213> ORGANISM: Brassica napus

<400> SEQUENCE: 74
tacggtgata atatgttaag tattatttaa ccaagttggt tattgtctgc taatagtttg       60
accattttgg aaccaatcat ttctcagtat gtttttcacct aacgtttttca ttgaagttta      120 gtaacgtaac tatcacagtt tttgacaaaa wgagactaat gccatcttta agaccttagt      180
taatctgaac tacttaaaac taagcaccta ttgtgaaaag tgaaaacaaa aagagtacga      240
tgatttcact tgtcatggtc tctttataca aaagcaaact caaaaacact atcaatgcca      300
a                                                                      301

<210> SEQ ID NO 75
<211> LENGTH: 301
<212> TYPE: DNA
<213> ORGANISM: Brassica napus

<400> SEQUENCE: 75
```

-continued

```
gattacttga cctcttgcct ggaaacatca ggaaacagag ctttgtttgt gtataaatat      60
acatgatcca aagtcctaac tagcccatct ttttaatctt tctggcattt ttcagcttgt     120
tcatgccttt acctgaacat cagttgaact rtcttctctg ttgtatatct gaccaagatt     180
tgatatgttg tttgcaattt gggtagcttc tggagaagga agatcctgca tttcataggt     240
atctttagag ccacttcttg tgatttaata tcaaaagctt cgtgtgagtc actttcatag     300
a                                                                     301

<210> SEQ ID NO 76
<211> LENGTH: 301
<212> TYPE: DNA
<213> ORGANISM: Brassica napus

<400> SEQUENCE: 76
acaaaataat gatttatatc ggctagtctc aaatcaaata taatttcaga ataaaaaaca      60
aactctactt agttgataac cgaactctaa taccatacat aaatttacat catattttgg     120
aaaaagtaaa agtatatgta taagttttaa kttagctaat tacccttagt tttaagtcaa     180
aactataaaa cagttttttat aaaagctttt ttatttttttt gggtttttgtt ttatataagg     240 aaaaacaaag aaaaacaaaa caccttcaat cgatattctc tattaaatca aaatttacca     300
c                                                                     301

<210> SEQ ID NO 77
<211> LENGTH: 121
<212> TYPE: DNA
<213> ORGANISM: Brassica napus

<400> SEQUENCE: 77
ttgggaaata aaaaagatag agtctacaag atgtatgtta tggttgttag ttccgatttg      60
yagagaaagc tcttatgaga aattggagac attctaacaa aagaaccaca aaaatatgca     120
t                                                                     121

<210> SEQ ID NO 78
<211> LENGTH: 121
<212> TYPE: DNA
<213> ORGANISM: Brassica napus

<400> SEQUENCE: 78
gttatgtata ataataaaac tattctcgtt catagtatca aatttcaaag attatttttg      60
rcttttcatt ttaatttggg aaataaaaaa gatagagtct acaagatgta tgttatggtt     120
g                                                                     121

<210> SEQ ID NO 79
<211> LENGTH: 301
<212> TYPE: DNA
<213> ORGANISM: Brassica napus

<400> SEQUENCE: 79
acagccacta agctcaagct tcacaagccc cttacaccct tgtgctaata tcgtcaaacc      60
aatatcggaa acagaagaag tatacagtcc ctccacgctt cccaccagtc tcaacactct     120
tagactctcg caagcagcga tgccacgtaa ratattatcg ttacacttgc ggagctcgag     180
ctcttgaaga tcggaacagt gctcggctaa accgagtaaa cctagctcag tagcgttagt     240
caccacgagc ttaagcaaat cgcagcttcc tcttcctaac accataagtc ctctgtcgat     300
t                                                                     301
```

-continued

```
<210> SEQ ID NO 80
<211> LENGTH: 301
<212> TYPE: DNA
<213> ORGANISM: Brassica napus

<400> SEQUENCE: 80
ctacaacaca ttccttttgt aagttatatt cgtcgctttc cacatccttt tccggtgact      60
taaactacaa gcctcgacga ggactgaccc ggtggtaaat ggaccttcta tacccacaga     120
ctctggaatt ttcagactcg cgcttgccct kaagttgcta ccgattcttc ttgtgcatcc     180
tccacctgcg tgtgttagac atcctccacc tgatgtctac gatctactat atttaaaata     240
tataagacaa aaaatacagc tcttcaaaat ttacattttg tatcatagac gaaaggcatc     300
c                                                                      301

<210> SEQ ID NO 81
<211> LENGTH: 121
<212> TYPE: DNA
<213> ORGANISM: Brassica napus

<400> SEQUENCE: 81
wgtacttgga gcttgggtac ggtgaatttt aaacgtttaa gttgtgtaga tgagtgaaac      60
mgaactggtt aagcttagct traaaacttt atatccaatg aatatttcca atattttcaa     120
t                                                                      121

<210> SEQ ID NO 82
<211> LENGTH: 121
<212> TYPE: DNA
<213> ORGANISM: Brassica napus

<400> SEQUENCE: 82
gataattgtt ggtttgattg tatgatgttt taatacttct ctattcattt atgccaactg      60
mtcatgawtt ttrtaattga aatcaaaagc atamtatacc tktgtttcat acatgactat     120
g                                                                      121

<210> SEQ ID NO 83
<211> LENGTH: 121
<212> TYPE: DNA
<213> ORGANISM: Brassica napus

<400> SEQUENCE: 83
caaatktrtc aaagtgattg rttttgtatc aaatgtgttg gtataattgt ttggtttgat      60
ytaaattggt ttagataatt gttggtttga ttgtatgatg ttttaatact tctctattca     120
t                                                                      121

<210> SEQ ID NO 84
<211> LENGTH: 301
<212> TYPE: DNA
<213> ORGANISM: Brassica napus

<400> SEQUENCE: 84
ggttttacgg tgatgtcgtt tcagagagtg aaaagtatcg gtggatgggt cctaaacgct      60
atgattatgt tggaactaaa gtattcttga agcacaggta tttcccttta acatatttac     120
caatttactc ttgccgagat gtgctgaaca stgttgggaa ctatgttaat gcaagatcat     180
atgaggcaga ggtgatgttt gaagaagcag agaacgctaa agcttcaccg ctcacgcgga     240
```

```
gcaagacatg gccatttcga agtacaacaa gatcagagaa gatactgtgt cgtgcaaaat      300
g                                                                     301

<210> SEQ ID NO 85
<211> LENGTH: 121
<212> TYPE: DNA
<213> ORGANISM: Brassica napus

<400> SEQUENCE: 85
aatatccgag tgggacttaa gagataggtt tggrtacaaa accaaatyga atcaaaattc       60
raattaagat ccgaaaattt ccgaaattag cttaatatgt tgatcttttg aagatttttaa     120 t                                                                     121

<210> SEQ ID NO 86
<211> LENGTH: 121
<212> TYPE: DNA
<213> ORGANISM: Brassica napus

<400> SEQUENCE: 86
tatctatctt cagatgcctg ttattattat attacagata atgttatgag taatgaagac       60
rcaatgtgga ctacccctaa aaatggataa actcatatgc ttgtatgtcg ttacaaatgc      120
a                                                                     121

<210> SEQ ID NO 87
<211> LENGTH: 1001
<212> TYPE: DNA
<213> ORGANISM: Brassica napus

<400> SEQUENCE: 87
aaatcaaaga ctgatgacct ctgccgagga atcttcccgg ccacgacaca ctcttcactc       60
ctgagattag aggagttata cagaggatca gttatctctc tcggttgatg agtctcaaaa      120
gcatccattt tggttatgat gcaaaggaga agagagagag agatgatatt ggtttgaata      180
ttactatgat ggtcatcacg acaacacttg acatttatta tattacagaa aatccctttg      240
acatttgact tcgtagctaa ttaaaagttc cttaaatgaa agaaatggtt acaagtgtca      300
tttgactttt gtagcatttg acttctagtt atctaagtcc agactttctg cctgagatca      360
tgaacgttca attaagaaga gagtttctgt tattatggga aggaagagaa acaaagacac      420
ttaaaacaag actcctaaac ctataattca atctctgtgg aatgaaccct ttcttctagg      480
ggaatgtaac attaaccttt yatcaaaatc atgatgctgt tggaactatc aggcatcttt      540
aaagaccagg aatagcctcc aggttatact tttcttcagc tttttgagct tcgccttccc      600
cactctctgg aggcggtttc ggcttctcca acgcatctag actctggcga tacacatagg      660
aagagctttg ccggttttta ctgctagaat tgcttatttg actagcaaga aaccttcgga      720 tgagcccct cagaaacgga gccaacgtat ctggttcatg ttctaggtaa tacattattc      780
ctcccataca tgcacagaac atagccacct gtttttcattg attgtataaa taaaaagatc      840
agttctattg ttaaagagga agaacggttg gtcccttgaa ttgtagtacc tcggcgtttt      900
taatatcagg aagaacgtgg cggttgacaa gtatctccca cagtgaatct cctgctcggg      960
gaagaacgta tagagcaagc tcagagcgtc tcggttttttt c                       1001

<210> SEQ ID NO 88
<211> LENGTH: 201
<212> TYPE: DNA
<213> ORGANISM: Brassica napus
```

-continued

```
<400> SEQUENCE: 88
aggaagagaa acaaagacac ttaaaacaag actcctaaac ctataattca atctctgtgg      60 aatgaacccct ttcttctagg ggaatgtaac attaacctttt yatcwaaatc atgatgctgt   120
tggamctatc aggcatcttt aaagaccagg aatagcctcc aggttatact tttcttcagc    180
tttttgagct tcgccttccc c                                                201

<210> SEQ ID NO 89
<211> LENGTH: 201
<212> TYPE: DNA
<213> ORGANISM: Brassica napus

<400> SEQUENCE: 89
ggttgacaag tatctcccac agtgaatctc ctgctcgggg aagaacgtat agagcaagct     60
cagagcgtct cggtttttttc tccagcataa ccgagagagc wgctacacca cccgcgaacc  120
agtaaacgat cttgtggtcc ttggwtgcaa cttttctatg kgcacatatg aaagcctatt    180
tgcaaatggg acataaagta t                                                201

<210> SEQ ID NO 90
<211> LENGTH: 401
<212> TYPE: DNA
<213> ORGANISM: Brassica napus
<220> FEATURE:
<221> NAME/KEY: misc_feature
<222> LOCATION: (86)..(86)
<223> OTHER INFORMATION: n is a A, T, C, or G
<220> FEATURE:
<221> NAME/KEY: misc_feature
<222> LOCATION: (316)..(316)
<223> OTHER INFORMATION: n is a A, T, C, or G

<400> SEQUENCE: 90
gttctttgtt ttggatggat gccattacat caaatgcatg acctgctcgt tctgttacaa     60
tcacctgatt tcaatggtaa atcaanaata tcaaactaag gacagttata gtatgcacag   120
cgagaaaaac acgtatgtct ttctgtatga gagttatatt atctaaagaa actatgcaat   180
gttgtagaga caaagaaaat ytcatttggc caacacaaca tctcagatag caaaaactgt    240
ggatatctac taaaacgcat aactactcac tttgcttcaa atgactacag aataaacaac   300
aaataactat tgatcnggac aaaccccaaa gaagcaaata caataaatgg taataacatt   360
ttcccctaat gctctaccat agcacacaat aataaatact c                        401

<210> SEQ ID NO 91
<211> LENGTH: 15
<212> TYPE: DNA
<213> ORGANISM: Artificial Sequence
<220> FEATURE:
<223> OTHER INFORMATION: synthetic oligonucleotide probe

<400> SEQUENCE: 91
ccaaatgaga ttttc                                                       15

<210> SEQ ID NO 92
<211> LENGTH: 15
<212> TYPE: DNA
<213> ORGANISM: Artificial Sequence
<220> FEATURE:
<223> OTHER INFORMATION: synthetic oligonucleotide probe

<400> SEQUENCE: 92
```

-continued

```
ccaaatgaaa ttttc                                              15

<210> SEQ ID NO 93
<211> LENGTH: 33
<212> TYPE: DNA
<213> ORGANISM: Artificial Sequence
<220> FEATURE:
<223> OTHER INFORMATION: synthetic oligonucleotide primer

<400> SEQUENCE: 93
tctaaagaaa ctatgcaatg ttgtagagac aaa                          33

<210> SEQ ID NO 94
<211> LENGTH: 27
<212> TYPE: DNA
<213> ORGANISM: Artificial Sequence
<220> FEATURE:
<223> OTHER INFORMATION: synthetic oligonucleotide primer

<400> SEQUENCE: 94
cacagttttt gctatctgag atgttgt                                 27

<210> SEQ ID NO 95
<211> LENGTH: 401
<212> TYPE: DNA
<213> ORGANISM: Brassica napus
<220> FEATURE:
<221> NAME/KEY: misc_feature
<222> LOCATION: (108)..(109)
<223> OTHER INFORMATION: n is A, T, C, or G
<220> FEATURE:
<221> NAME/KEY: misc_feature
<222> LOCATION: (111)..(112)
<223> OTHER INFORMATION: n is A, T, C, or G
<220> FEATURE:
<221> NAME/KEY: misc_feature
<222> LOCATION: (169)..(169)
<223> OTHER INFORMATION: n is A, T, C, or G
<220> FEATURE:
<221> NAME/KEY: misc_feature
<222> LOCATION: (239)..(239)
<223> OTHER INFORMATION: n is A, T, C, or G

<400> SEQUENCE: 95
ggcgccagcc tttgcctgta ccggttaggg tcctgggcac gtctccccgc cctgcgaatc    60
gaacagctga cctccccaag gcgcagatac cactggacta tcgagtcnng nnagtagcaa   120
cataactaac aagttaaact ccaatattca tgataatatg ttactatana gtcgtcgtat   180
gaataagaaa atgagagcat kcatatttgt attattttaa ttagtacaag caaattaana   240
ggagatgatt aatcgttgct tttgttgcgt cgcatgtgtg attacttcaa acgtggcagc   300
attttggata tgtcgtcctc tgtcgttaaa ttagggttta aatggagttg ttttcgtttc   360
atgaatttat tacacatatt acgttggacc ttcatgttct a                      401

<210> SEQ ID NO 96
<211> LENGTH: 18
<212> TYPE: DNA
<213> ORGANISM: Artificial Sequence
<220> FEATURE:
<223> OTHER INFORMATION: synthetic oligonucleotide probe

<400> SEQUENCE: 96
atgagagcat tcatattt                                           18

<210> SEQ ID NO 97
<211> LENGTH: 17
```

-continued

```
<212> TYPE: DNA
<213> ORGANISM: Artificial Sequence
<220> FEATURE:
<223> OTHER INFORMATION: synthetic oligonucleotide probe

<400> SEQUENCE: 97
tgagagcatg catattt                                                  17

<210> SEQ ID NO 98
<211> LENGTH: 34
<212> TYPE: DNA
<213> ORGANISM: Artificial Sequence
<220> FEATURE:
<223> OTHER INFORMATION: synthetic oligonucleotide primer

<400> SEQUENCE: 98
gcaacataac taacaagtta aactccaata ttca                               34

<210> SEQ ID NO 99
<211> LENGTH: 25
<212> TYPE: DNA
<213> ORGANISM: Artificial Sequence
<220> FEATURE:
<223> OTHER INFORMATION: synthetic oligonucleotide primer

<400> SEQUENCE: 99
acgcaacaaa agcaacgatt aatca                                         25

<210> SEQ ID NO 100
<211> LENGTH: 590
<212> TYPE: DNA
<213> ORGANISM: Brassica napus

<400> SEQUENCE: 100
gaggctattg gtgtccatgg ggttatctta caatgagctc aacagtccgt ccccaagtgg    60
aaatcaactg aatcttaatg aagcaacagm aycttgttcc ctgccaacca cagactgtct   120
gcttgtcgct tacgagtgag tatcatttat tgctataata ttattctctc aatgatcata   180
gcctttgaaa aatgactttt atgggaagtg gacagggaaa atatttgttg atgaataacg   240
gtaggggtct tttattatga tgattgcaag agctagatag tgctaaatac tgttgcttcc   300
caacctctga catattataa tgacatttgc ttgtgtgaat tgcttttttt tatgctcttt   360
ggatcttttc atgctaagaa acataccttt atctattctt gttcaacatt ttcggctaaa   420
ctgttctttt ggagagtagg caagctagct aactagttct tgctatttta ttctaggcgc   480
atttctccat cttttcctgt ggagaatttc agcgtcattg tagaatatgg aggtccaaat   540
gcatcgccca gagtctcatc tcctttaaag ttggactcct ttccttgctt              590
```

SNP MARKERS AND SELECTION OF LOW FIBER IN BRASSICA

CROSS REFERENCE TO RELATED APPLICATIONS

This application is a 35 U.S.C. § 371 national stage application of PCT International Application No. PCT/US2019/066135 filed Dec. 13, 2019, which claims the benefit of U.S. Provisional Patent Application Ser. No. 62/782,699, filed Dec. 20, 2018, the disclosures of which are incorporated by reference herein in their entirety.

TECHNICAL FIELD

The disclosure relates to fine mapping of quantitative trait loci (QTL) associated with desirable nutritional traits in canola (*Brassica napus*), including low fiber content. Additional embodiments relate to compositions and methods for identifying a low fiber content trait in canola using molecular markers tightly linked to low fiber content. Further embodiments relate to compositions and methods for introducing a low fiber content trait into canola by using these molecular markers.

BACKGROUND

Canola (*Brassica napus* L., 2n=4x=38, AACC), an allotetraploid formed from diploids B. raga (2n=2x=20, AA) and *B. oleracea* (2n=2x=18, CC), is one of the most important vegetable oilseed crops in the world, especially in China, Canada, the European Union and Australia. Canola meal, the fraction of the seed remaining after crushing and oil extraction, is approximately 55% of the volume of canola seed.

Canola meal consists of several components including protein, fiber, residual oil, carbohydrates, and anti-nutritional factors. Although canola meal is relatively high in protein, its high fiber content decreases its digestibility and its value as an animal feed. Compared to soybean meal, canola meal contains higher values of dietary fiber and a lower percentage of protein. Because of its high dietary fiber, canola meal has about 20% less metabolizable energy (ME) than soybean meal. As a result, the value of the meal has remained low relative to other oilseed meals such as soybean meal, particularly in rations for pigs and poultry. Rakow (2004a) *Canola meal quality improvement through the breeding of yellow-seeded varieties —an historical perspective, in AAFC Sustainable Production Systems Bulletin.* Additionally, the presence of glucosinolates in some canola meals also decreases its value, due to the deleterious effects these compounds have on the growth and reproduction of livestock.

Canola varieties are distinguished in part by their seed coat color. Seed coat color is generally divided into two main classes: yellow and black (or dark brown). Varying shades of these colors, such as reddish brown and yellowish brown, are also observed. Canola varieties with lighter seed coat color have been widely observed to have thinner hulls, and thus less fiber and more oil and protein than varieties with dark color seed coats. Stringam et al. (1974) Chemical and morphological characteristics associated with seed coat color in rapeseed, in *Proceedings of the 4th International Rapeseed Congress*, Giessen, Germany, pp. 99-108; Bell and Shires (1982) Can. J. Animal Science 62:557-65; Shirzadegan and Röbbelen (1985) Götingen Fette Seifen Anstrichmittel 87:235-7; Simbaya et al. (1995) J. Agr. Food Chem. 43:2062-6; Rakow (2004b) *Yellow-seeded Brassica*

*napus canola for the Canadian canola industry*, in *AAFC Sustainable Production Systems Bulletin*. One possible explanation for this is that the canola plant may expend more energy into the production of proteins and oils if it does not require that energy for the production of seed coat fiber components. Yellow-seeded canola lines also have been reported to have lower glucosinolate content than black-seeded canola lines. Rakow et al. (1999b) Proc. 10th Int. Rapeseed Congress, Canberra, Australia, Sep. 26-29, 1999, Poster #9. Thus, historically the development of yellow-seeded canola varieties has been pursued as a potential way to increase the feed value of canola meal. Bell (1995) *Meal and by-product utilization in animal nutrition*, in *Brassica oilseeds, production and utilization*. Eds. Kimber and McGregor, Cab International, Wallingford, Oxon, OX108DE, UK, pp. 301-37; Rakow (2004b), supra; Rakow & Raney (2003).

Some yellow-seeded forms of *Brassica* species closely related to *B. napus* (e.g., *B. rapa* and *B. juncea*) have been shown to have lower levels of fiber in their seed and subsequent meal. Scientists at Agriculture and Agri-Foods Canada (AAFC) have developed yellow seed coat (YSC) lines (YN86-37, YN90-1016, YN97-262 and YN01-429) of low hull proportion with thinner seed coat, low fiber and high oil compared to the black seed coat (BSC) canola (Rakow et al., 2011). Feeding studies, comparing yellow seeded canola meal from AAFC line YN01-429 to *B. juncea*, *B. rapa*, and brown-seeded *B. napus*, demonstrated the advantages of YSC *B. napus* line such as higher protein, lower fiber, increased amino acid digestibility and metabolizable energy content, and improved nutrient and energy utilization based on feed to gain ratio in broiler chickens and monogastric animal species (Hickling, 2009; Slominski et al., 2010).

The development of yellow-seeded *B. napus* germplasm has demonstrated that fiber can be reduced in *B. napus* through the integration of genes controlling seed pigmentation from related *Brassica* species. However, the breeding of low fiber content has been greatly hampered by a poor understanding of the inheritance and stability of the low fiber content traits, as well as a lack of robust, high-throughput markers tightly linked to the trait. Due to allotetraploidy, effect of multiple genes, maternal effects and environmental effects, the inheritance of low fiber content trait is complex, and identification of markers tightly linked to this trait is very challenging. Current selection of lower fiber canola lines derived from the AAFC YSC lines has primarily been based on fiber content data obtained using cost and labor intensive analytical methods, or seed coat color, because of its high correlation with low fiber in the AAFC YSC lines.

Very little information is available as to how much variability there is for fiber within dark-seeded *B. napus* germplasm, and limited reports have been made of dark-seeded canola lines having been developed that contain reduced levels of anti-nutritional factors (e.g., fiber and polyphenolic compounds), and increased protein levels. One such example are *B. napus* open pollinated cultivars (CL044864, CL065620) and hybrids (CL166102H, CL121460H and CL121466H) which comprise favorable seed composition characteristics, including high protein content, low fiber content, reduced polyphenolic content and increased phosphorous content (U.S. Pat. No. 9,596,871 B2). These desirable nutritional characteristics make this germplasm particularly valuable as sources for canola meal. However, molecular markers that are tightly linked to this desirable nutritional trait in dark-seeded canola lines have not been previously described.

BRIEF SUMMARY OF THE INVENTION

Described herein is a method for identifying a quantitative trait locus (QTL) associated with desirable nutritional traits, including low fiber content in canola. The method includes providing or isolating a nucleic acid sample from a *Brassica napus* plant or germplasm thereof and screening the sample for a nucleic acid comprising one or more low fiber content marker alleles located within a chromosome interval on *Brassica napus* chromosome N13. One terminus of the N13 chromosomal interval is defined by and includes base pair (bp) position 7301735 (DBSNP143552; SEQ ID NO:1) and the other N13 interval terminus is defined by and includes bp position 9417330 (DBSNP243314; SEQ ID NO:89). For example, the marker allele used to screen for the low fiber content trait can be one or more allele marker alleles of SEQ ID NOs:1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 95, or 100. In certain examples, the method includes obtaining a nucleic acid sample from a *Brassica napus* plant or germplasm and screening the sample for a nucleic acid sample comprising the low fiber content marker allele SEQ ID NO:90, SEQ ID NO:95 or both SEQ ID Nos:90 and 95. In another example, the method can include screening the sample for a nucleic acid comprising one or more low fiber content marker alleles located within a smaller chromosome interval on *Brassica napus* chromosome N13, such that one terminus of the N13 interval is defined by and includes bp position 8978949 (DBSNP02056, SEQ ID NO:61) and the other interval terminus is defined by and includes bp position 9375623 (DBSNP243323, SEQ ID NO: 77). Thus, the method can include screening the smaller interval for one or more low fiber content marker trait alleles of SEQ ID NOs:61, 62, 63, 64, 65, 66, 67, 68, 69, 70, 71, 72, 73, 74, 75, 76, 77, or 100. See Examples 1-3 herein, including Table 3, for additional details regarding N13 intervals and markers used in the disclosed methods.

Each of the foregoing methods can be used to screen for one or more of the disclosed chromosome N13 low fiber content marker alleles from *Brassica napus* line CL044864. Each of the foregoing disclosed methods can be used to screen for one or more of the disclosed chromosome N13 low fiber content marker alleles from *Brassica napus* line CL065620 or its lineage. Screening for the presence of one or more low fiber content marker alleles in accordance with the methods disclosed herein can be done using techniques such as allele-specific polymerase chain reaction (PCR) amplification or nucleic acid sequencing.

In a particular example, the disclosed method for identifying a plant, or germplasm thereof, includes providing or isolating a nucleic acid sample from a *Brassica napus* plant or germplasm and screening the sample for a nucleic acid that comprises one or more chromosome N13 low fiber content marker alleles using a nucleic acid probe comprising SEQ ID NO:91, SEQ ID NO:92, SEQ ID NO 96, or SEQ ID NO:97, or a combination of the foregoing probes. See, e.g., Example 3 herein.

This disclosure provides seed from a *Brassica napus* plant identified by a method disclosed herein as having one or more chromosome N13 low fiber content marker alleles disclosed herein. This disclosure further provides meal made from such seed of a plant identified as having the one or more chromosome N13 low fiber content marker alleles.

Also provided herein is a method for selecting one or more plants, or germplasm thereof, from a population, wherein the selected plant comprises a quantitative trait locus (QTL) associated with desirable nutritional traits, including low fiber content in canola. The method includes obtaining or isolating a nucleic acid sample from each plant, or germplasm thereof, in a plurality of plants within a population of *Brassica napus* plants, screening each sample for a nucleic acid comprising one or more low fiber content marker alleles located within *Brassica napus* chromosome N13 interval defined by and including bp position 7301735 (DBSNP143552; SEQ ID NO:1) to bp position 9417330 (DBSNP243314; SEQ ID NO:89), wherein the one or more marker alleles are indicative of low fiber content in *Brassica napus*. The method includes then selecting one or more plants, or germplasm thereof, from the population which are identified by the screening step as having the one or more low fiber content marker alleles. For example, the one or more marker alleles used to screen for the low fiber content trait can be one or more allele marker alleles of SEQ ID NOs:1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 95, or 100; and each of the selected one or more plants, or germplasm thereof, has the foregoing screened-for one or more low fiber content marker alleles. In certain examples, the method of selection includes obtaining a nucleic acid sample from a *Brassica napus* plant or germplasm and screening the sample for a nucleic acid sample comprising the low fiber content marker allele SEQ ID NO:90, SEQ ID NO:95, or both SEQ ID NOs:90 and 95; and the selected one or more plants, or germplasm thereof, includes one or both of these screened-for low fiber content marker alleles. In one aspect, the disclosed method of selection can include screening each sample for a nucleic acid comprising one or more low fiber content marker alleles located within a smaller chromosome N13 interval defined by and including bp position 8978949 (DBSNP02056, SEQ ID NO:61) to other terminus is defined by and includes bp position 9375623 (DBSNP243323, SEQ ID NO:77); and the method includes selecting one or more plants, or germplasm thereof, having the screened-for one or more low fiber content marker alleles. For example, the selection method can include screening the smaller interval for one or more low fiber content marker trait alleles of SEQ ID NOs:61, 62, 63, 64, 65, 66, 67, 68, 69, 70, 71, 72, 73, 74, 75, 76, 77, or 100; and each of the selected one or more plants, or germplasm thereof, has the screened-for one or more low fiber content marker alleles of SEQ ID NOs:61, 62, 63, 64, 65, 66, 67, 68, 69, 70, 71, 72, 73, 74, 75, 76, 77, or 100.

In each of the foregoing disclosed methods of selection, the one or more chromosome N13 low fiber content marker alleles that is screened for and found in each selected plant, or germplasm thereof, can be one or more marker alleles from *Brassica napus* line CL044864. Additionally or alternatively in each of the foregoing disclosed methods of selection, the one or more chromosome N13 low fiber content marker alleles that is screened for and found in each selected plant, or germplasm thereof, can be one or more marker alleles from *Brassica napus* line CL065620 or its lineage. Moreover, in the disclosed methods of selecting one or more plants, or germplasm thereof, in a plurality of plants within a population of *Brassica napus* plants, the step of screening each sample for a nucleic acid comprising one or more low fiber content marker alleles can be done using techniques such as allele-specific polymerase chain reaction (PCR) amplification or nucleic acid sequencing.

In a particular example of the disclosed method for selecting a *Brassica napus* plant or germplasm, the method includes providing or isolating a nucleic acid sample from a *Brassica napus* plant or germplasm thereof, screening each sample for a nucleic acid having one or more chromosome N13 low fiber content marker alleles using a nucleic acid probe comprising SEQ ID NO:91, SEQ ID NO:92, SEQ ID NO 96, or SEQ ID NO:97, or a combination of the foregoing probes.

This disclosure also provides seed from a *Brassica napus* plant selected as having the one or more chromosome N13 low fiber content marker alleles in accordance with any one of the methods for selecting a plant described herein. This disclosure further provides meal made from such seed of a plant selected as having the one or more chromosome N13 low fiber content marker alleles.

In another embodiment, disclosed herein is a method for producing a canola plant or germplasm that comprises a quantitative trait locus (QTL) associated with desirable nutritional traits, including low fiber content in canola. The method includes obtaining or isolating a nucleic acid sample from each of one or more *Brassica napus* plants or germplasm thereof, screening each sample for a nucleic acid comprising one or more low fiber content marker alleles located within *Brassica napus* chromosome N13 interval defined by and including bp position 7301735 (DBSNP143552; SEQ ID NO:1) to bp position 9417330 (DBSNP243314; SEQ ID NO:89), wherein the one or more marker alleles are indicative of low fiber content in *Brassica napus*. The method further includes selecting a first *Brassica napus* plant which is identified by the screening step as having the screened-for one or more low fiber content marker alleles, and then crossing the selected first plant with a second plant to produce progeny plants, wherein at least one of the progeny plants comprises the screened-for one or more low fiber content marker alleles. For example, the one or more marker alleles used to screen for the low fiber content trait can be one or more allele marker alleles of SEQ ID NOs:1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 95, or 100; such that the selected first plant and at least one progeny plant comprise the foregoing screened-for one or more low fiber content marker alleles. In certain examples of the disclosed method of producing a canola plant, the method includes screening each sample for a nucleic acid sample comprising the low fiber content marker allele SEQ ID NO:90, SEQ ID NO:95, or both SEQ ID Nos:90 and 95; such that the selected first plant and at least one progeny plant comprise one or both of these screened-for low fiber content marker alleles. In one aspect, the disclosed method of producing a canola plant includes screening each sample for a nucleic acid comprising one or more low fiber content marker alleles located within a smaller chromosome chromosome N13 interval defined by and including bp position 8978949 (DBSNP02056, SEQ ID NO:61) to bp position 9375623 (DBSNP243323, SEQ ID NO:77); and the selected first *Brassica napus* plant and at least one progeny plant comprise the screened-for one or more low fiber content marker alleles within the smaller N13 interval. For example, the method of producing a canola plant can include screening the smaller interval for one or more low fiber content marker trait alleles of SEQ ID NOs:61, 62, 63, 64, 65, 66, 67, 68, 69, 70, 71, 72, 73, 74, 75, 76, 77, or 100; such that the selected first *Brassica napus* plant and at least one progeny plant has the screened-for one or more low fiber content marker alleles of SEQ ID NOs:61, 62, 63, 64, 65, 66, 67, 68, 69, 70, 71, 72, 73, 74, 75, 76, 77, or 100.

In each of the foregoing disclosed methods for producing a canola plant, the one or more chromosome N13 low fiber content marker alleles that is screened for and found in the first *Brassica napus* plant and at least one progeny plant can be one or more marker alleles from *Brassica napus* line CL044864. Additionally or alternatively in each of the foregoing disclosed methods of producing a canola plant, the one or more chromosome N13 low fiber content marker alleles that is screened for and found in the first *Brassica napus* plant and at least one progeny plant can be one or more marker alleles from *Brassica napus* line CL065620 or its lineage. Moreover, in the disclosed methods of producing a canola plant, the step of screening each sample for a nucleic acid comprising one or more low fiber content marker alleles can be done using techniques such as allele-specific polymerase chain reaction (PCR) amplification or nucleic acid sequencing.

In a particular example, a disclosed method for producing a canola includes providing or isolating a nucleic acid sample from each of one or more *Brassica napus* plants or germplasm thereof, screening each sample for a nucleic acid comprising one or more chromosome N13 low fiber content marker alleles using a nucleic acid probe comprising SEQ ID NO:91, SEQ ID NO:92, SEQ ID NO 96, or SEQ ID NO:97, or a combination of the foregoing probes.

This disclosure also provides seed from a *Brassica napus* progeny plant which has one or more chromosome N13 low fiber and which is produced according to any one of the methods described herein for producing a canola plant having a low fiber content trait. This disclosure further provides meal made from such seed of a plant having the one or more chromosome N13 low fiber content marker alleles.

Also described are methods of producing a canola plant or germplasm that include the low fiber content trait. Such methods may include introgressing at least one low fiber content marker from a first canola plant into a second canola plant thereby producing progeny canola plant or germplasm thereof having the low fiber content marker. The introgressed marker is located within the chromosome N13 interval defined by and including bp position 7301735 (DBSNP143552; SEQ ID NO:1) to bp position 9417330 (DBSNP243314; SEQ ID NO:89) and linked to the low fiber content trait in the first canola plant. For example, the introgressed marker can be located within the smaller chromosome N13 interval defined by and including bp position 8978949 (DBSNP02056, SEQ ID NO:61) to bp position 9375623 (DBSNP243323, SEQ ID NO:77), wherein the marker is linked to the low fiber content trait in the first canola plant. The introgression process may comprise any of the foregoing methods disclosed herein for identifying, selecting, or producing a *Brassica napus* plant comprising one or more of the low fiber content marker alleles located within the chromosome N13 interval. In certain examples of the disclosed method of introgressing, the first plant that comprises the low fiber content marker within the chromosome N13 interval is crossed with a second plant that does not comprise the low fiber content marker to produce the progeny plant, which has lower fiber content relative to the second plant.

The foregoing and other features will become more apparent from the following detailed description of several embodiments.

BRIEF DESCRIPTION OF THE DRAWINGS

FIG. 1. Genetic map of the 6.2 cM chromosomal interval on N13 where the low fiber content QTL is located. Position 0.0 of the genetic map shown in FIG. 1 corresponds to 32.4 cM on Table 3.

SEQUENCE LISTING

The nucleic acid sequences listed in the accompanying sequence listing are shown using standard letter abbreviations for nucleotide bases, as defined in 37 C.F.R. § 1.822. Only one strand of each nucleic acid sequence is shown, but the complementary strand is understood to be included by any reference to the displayed strand. In the accompanying sequence listing:

SEQ ID NOs:1-90, 95, and 100 are the marker sequences linked to the low fiber content QTL found in the chromosomal interval on N13.

SEQ ID NOs:91-94 are the TAQMAN™ assay primers and probes for SNP marker n13:58387757 (SEQ ID NO:90).

SEQ ID NOs:96-99 are the TAQMAN™ assay primers and probes for SNP marker n13_59498877 (SEQ ID NO:95).

DETAILED DESCRIPTION OF THE INVENTION

I. Overview of Several Embodiments

The invention provides high-throughput single nucleotide polymorphism (SNP) markers and high-density genetic maps for fine mapping and validation of a quantitative trait locus (QTL) underlying a low fiber content trait derived from black-seeded canola (BSC) lines. In particular examples, the BSC lines may be lines CL044864 and CL065620 and their lineages. The SNP markers are tightly linked to the low fiber content trait and may be used for marker-assisted selection (MAS) of the low fiber content trait.

According to the invention, these SNP markers may be used to introgress a low fiber content trait, e.g., from the BSC sources described above, into agronomically desirable canola species and cultivars (for example, to overcome the lack of low fiber content in cultivated canola). It is desirable for a number of reasons to produce a canola plant having decreased fiber content, when compared to a conventional variety. Thus, the methods disclosed herein can be used in high-throughput and cost-effective strategies and processes for the design and execution of low fiber content introgression programs for canola.

In some aspects, the invention provides compositions and methods for identifying, selecting and/or producing canola plants having the low fiber content trait from BSC lines CL044864 and CL065620 and their lineages, as well as canola plants, parts thereof, including but not limited to seeds, and canola germplasm, that are identified, selected and/or produced by methods of this invention. The present invention further provides an assay for the detection of the low fiber trait in a canola plant, plant part and/or canola germplasm.

The present invention provides a method of leveraging SNP markers and high-density genetic maps based on the low fiber content trait from BSC lines CL044864 and CL065620, using an extensive set of phenotypic data from four dihaploid (DH) populations. The present invention is based, at least in part, on the discovery of a major QTL on N13 that explains 65.9% to 71.5% of the variance of a fiber content trait in two DH populations. This major QTL on N13 was validated and confirmed to be different from the low fiber content QTL from YSC line YN01-429 on N09 (U.S. patent application Ser. No. 15/731,561) in two DH populations.

The disclosed invention also provides canola marker loci and a QTL chromosome interval that demonstrate statistically significant co-segregation with (and therefore are predictive and determinative of) low fiber content. For example, 92 canola marker loci (SEQ ID NOs:1-90, 95 and 100) within a 6.2 cM interval or 2,115,595 bp on chromosome N13 on the proprietary *B. napus* reference genome, DH12075 are disclosed. The interval can further be defined by its location on chromosome N13 from bp position 7,301,735 to bp position 9,417,330 on the *B. napus* reference genome, DH12075, comprising and flanked by DBSNP143552 (SEQ ID NO:1) and DBSNP243314 (SEQ ID NO:89). In particular examples, markers within this interval may be used for marker-assisted selection of the low fiber content trait from BSC lines CL044864 and CL065620 and their lineages, and thus may improve the breeding process of canola lines with low fiber content.

The invention also provides methods for identifying a first canola plant or germplasm that displays low fiber content. In some examples, at least one allele of one or more marker loci that is linked (e.g., tightly-linked) with a low fiber content trait from the CL044864 or CL065620 lines or their lineages, is/are detected in the first canola plant or germplasm. In some examples, the marker loci may be selected from the loci in Table 3, including SEQ ID NOs: 1-90, 95, and 100.

II. Terms

Allotetraploid: As used herein, "allotetraploid" generally refers to a hybrid organism that has a chromosome set that is four times that of a haploid organism.

Isolated: An "isolated" biological component (such as a nucleic acid or protein) has been substantially separated, produced apart from, or purified away from other biological components in the cell of the organism in which the component naturally occurs (i.e., other chromosomal and extra-chromosomal DNA and RNA, and proteins), while effecting a chemical or functional change in the component. For example and without limitation, a nucleic acid may be isolated from a chromosome by breaking chemical bonds connecting the nucleic acid to the remaining DNA in the chromosome. Nucleic acid molecules and proteins that have been "isolated" include nucleic acid molecules and proteins purified by standard purification methods. The term also embraces nucleic acids and proteins prepared by recombinant expression in a host cell, as well as chemically-synthesized nucleic acid molecules, proteins, and peptides.

Nucleic acid molecule: As used herein, the term "nucleic acid molecule" may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide." The term includes single- and double-stranded forms of DNA. A nucleic acid molecule can include either or both naturally occurring and modified nucleotides, linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, inter-nucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and pad-locked conformations.

Mapping population: As used herein, the term "mapping population" may refer to a plant population (e.g., a canola plant population) used for genetic mapping. Mapping populations are typically obtained from controlled crosses of parent genotypes, as may be provided by two inbred lines. Decisions on the selection of parents, mating design for the development of a mapping population, and the type of markers used depend upon the gene to be mapped, the availability of markers, and the molecular map. The parents of plants within a mapping population should have sufficient variation for a trait(s) of interest at both the nucleic acid sequence and phenotype level. Variation of the parents' nucleic acid sequence is used to trace recombination events in the plants of the mapping population.

The availability of informative polymorphic markers is dependent upon the amount of nucleic acid sequence variation. Thus, a particular informative marker may not be identified in a particular cross of parent genotypes, though such markers may exist.

A "genetic map" is a description of genetic linkage relationships among loci on one or more chromosomes (or linkage groups) within a given species, as may be determined by analysis of a mapping population. In some examples, a genetic map may be depicted in a diagrammatic or tabular form. The term "genetic mapping" may refer to the process of defining the linkage relationships of loci through the use of genetic markers, mapping populations segregating for the markers, and standard genetic principles of recombination frequency. A "genetic map location" refers to a location on a genetic map (relative to surrounding genetic markers on the same linkage group or chromosome) where a particular marker can be found within a given species. In contrast, a "physical map of the genome" refers to absolute distances (for example, measured in base pairs or isolated and overlapping contiguous genetic fragments) between markers within a given species. A physical map of the genome does not necessarily reflect the actual recombination frequencies observed in a test cross of a species between different points on the physical map.

Cross: As used herein, the term "cross" (or "crossed") refers to the fusion of gametes via pollination to produce progeny (e.g., cells, seeds, and plants). This term encompasses both sexual crosses (i.e., the pollination of one plant by another) and selling (i.e., self-pollination, for example, using pollen and ovule from the same plant).

Backcrossing: Backcrossing methods may be used to introduce a nucleic acid sequence into plants. The backcrossing technique has been widely used for decades to introduce new traits into plants. Jensen, N., Ed. Plant Breeding Methodology, John Wiley & Sons, Inc., 1988. In a typical backcross protocol, the original variety of interest (recurrent parent) is crossed to a second variety (non-recurrent parent) that carries a gene of interest to be transferred. The resulting progeny from this cross are then crossed again to the recurrent parent, and the process is repeated until a plant is obtained wherein essentially all of the desired morphological and physiological characteristics of the recurrent plant are recovered in the converted plant, in addition to the transferred gene from the nonrecurrent parent.

Introgression: As used herein, the term "introgression" refers to the transmission of an allele at a genetic locus into a genetic background. In some embodiments, introgression of a specific allele form at the locus may occur by transmitting the allele form to at least one progeny via a sexual cross between two parents of the same species, where at least one of the parents has the specific allele form in its genome. Progeny comprising the specific allele form may be repeatedly backcrossed to a line having a desired genetic background. Backcross progeny may be selected for the specific allele form, so as to produce a new variety wherein the specific allele form has been fixed in the genetic background. In some embodiments, introgression of a specific allele form may occur by recombination between two donor genomes (e.g., in a fused protoplast), where at least one of the donor genomes has the specific allele form in its genome. Introgression may involve transmission of a specific allele form that may be, for example and without limitation, a selected allele form of a marker allele; a QTL; and/or a transgene. In this disclosure, introgression may involve transmission of one or more of the disclosed low fiber content marker alleles (e.g., disclosed in Table 3 herein) into a progeny plant.

Germplasm: As used herein, the term "germplasm" refers to genetic material of or from an individual plant or group of plants (e.g., a plant line, variety, and family), and a clone derived from a plant or group of plants. A germplasm may be part of an organism or cell, or it may be separate (e.g., isolated) from the organism or cell. In general, germplasm provides genetic material with a specific molecular makeup that is the basis for hereditary qualities of the plant. As used herein, "germplasm" refers to cells of a specific plant; seed; tissue of the specific plant (e.g., tissue from which new plants may be grown); and non-seed parts of the specific plant (e.g., leaf, stem, pollen, and cells).

As used herein, the term "germplasm" is synonymous with "genetic material," and it may be used to refer to seed (or other plant material) from which a plant may be propagated. A "germplasm bank" may refer to an organized collection of different seed or other genetic material (wherein each genotype is uniquely identified) from which a known cultivar may be cultivated, and from which a new cultivar may be generated. In embodiments, a germplasm utilized in a method or plant as described herein is from a canola line or variety. In particular examples, a germplasm is seed of the canola line or variety. In particular examples, a germplasm is a nucleic acid sample from the canola line or variety.

Gene: As used herein, the term "gene" (or "genetic element") may refer to a heritable genomic DNA sequence with functional significance. The term "gene" may also be used to refer to, for example and without limitation, a cDNA and/or an mRNA encoded by a heritable genomic DNA sequence.

Genotype: As used herein, the term "genotype" refers to the genetic constitution of an individual (or group of individuals) at one or more particular loci. The genotype of an individual or group of individuals is defined and described by the allele forms at the one or more loci that the individual has inherited from its parents. The term genotype may also be used to refer to an individual's genetic constitution at a single locus, at multiple loci, or at all the loci in its genome. A "haplotype" is the genotype of an individual at a plurality of genetic loci. In some examples, the genetic loci described by a haplotype may be physically and genetically linked; i.e., the loci may be positioned on the same chromosome segment.

Elite line: As used herein, the term "elite line" means any line that has resulted from breeding and selection for superior agronomic performance. An elite plant is any plant from an elite line.

Quantitative trait: As used herein, a "quantitative trait" may refer to a trait or phenotype that is expressed in varying degrees, along a generally continuous gradient and is frequently linked to two or more genes and is affected by environment.

Quantitative trait locus or QTL: As used herein, a "quantitative trait locus" refers to a segment or region of DNA containing or linked to a gene or genes underlying a quantitative trait.

As used herein, the term "QTL interval" may refer to stretches of DNA that are linked to the gene(s) that underlie the QTL trait. A QTL interval is typically, but not necessarily, larger than the QTL itself. A QTL interval may contain stretches of DNA that are 5' and/or 3' with respect to the QTL.

Multiple experimental paradigms have been developed to identify and analyze QTLs. See, e.g., Jansen (1996) Trends Plant Sci. 1:89. The majority of published reports on QTL mapping in crop species have been based on the use of a bi-parental cross. See Lynch and Walsh (1997) Genetics and Analysis of Quantitative Traits, Sinauer Associates, Sunderland. Typically, these paradigms involve crossing one or more parental pairs that can be, for example, a single pair derived from two inbred strains, or multiple related or unrelated parents of different inbred strains or lines, which each exhibit different characteristics relative to the phenotypic trait of interest. Typically, this experimental protocol involves deriving 100 to 300 segregating progeny from a single cross of two divergent inbred lines that are, for example, selected to maximize phenotypic and molecular marker differences between the lines. The parents and segregating progeny are genotyped for multiple marker loci, and evaluated for one to several quantitative traits (e.g., low fiber content). QTLs are then identified as significant statistical associations between genotypic values and phenotypic variability among the segregating progeny.

Numerous statistical methods for determining whether markers are genetically linked to a QTL (or to another marker) are known to those of skill in the art and include, for example and without limitation, standard linear models (e.g., ANOVA or regression mapping; Haley and Knott (1992) Heredity 69:315); and maximum likelihood methods (e.g., expectation-maximization algorithms; Lander and Botstein (1989) Genetics 121:185-99; Jansen (1992) Theor. Appl.

Genet. 85:252-60; Jansen (1993) Biometrics 49:227-31; Jansen (1994) "Mapping of quantitative trait loci by using genetic markers: an overview of biometrical models," In J. W. van Ooijen and J. Jansen (eds.), Biometrics in Plant breeding: applications of molecular markers, pp. 116-24, CPRO-DLO Netherlands; Jansen (1996) Genetics 142:305-11; and Jansen and Stam (1994) Genetics 136:1447-55).

Exemplary statistical methods include single point marker analysis; interval mapping (Lander and Botstein (1989) Genetics 121:185); composite interval mapping; penalized regression analysis; complex pedigree analysis; MCMC analysis; MQM analysis (Jansen (1994) Genetics 138:871); HAPLO-IM+ analysis, HAPLO-MQM analysis, and HAPLO-MQM+ analysis; Bayesian MCMC; ridge regression; identity-by-descent analysis; and Haseman-Elston regression, any of which are suitable in the context of particular embodiments of the invention. Alternative statistical methods applicable to complex breeding populations that may be used to identify and localize QTLs in particular examples are described in U.S. Pat. No. 6,399,855 and PCT International Patent Publication No. W00149104 A2. All of these approaches are computationally intensive and are usually performed with the assistance of a computer-based system comprising specialized software. Appropriate statistical packages are available from a variety of public and commercial sources, and are known to those of skill in the art.

Marker: Although specific DNA sequences that encode proteins are generally well-conserved across a species, other regions of DNA (e.g., non-coding DNA and introns) tend to develop and accumulate polymorphism, and therefore may be variable between individuals of the same species. The genomic variability can be of any origin, for example, the variability may be due to DNA insertions, deletions, duplications, repetitive DNA elements, point mutations, recombination events, and the presence and sequence of transposable elements. Such regions may contain useful molecular genetic markers. In general, any differentially inherited polymorphic trait (including nucleic acid polymorphisms) that segregates among progeny is a potential marker.

As used herein, the terms "marker" and "molecular marker" refer to a nucleic acid or encoded product thereof (e.g., a protein) used as a point of reference when identifying a linked locus. Thus, a marker may refer to a gene or nucleic acid that can be used to identify plants having a particular allele. A marker may be described as a variation at a given genomic locus. A genetic marker may be a short DNA sequence, such as a sequence surrounding a single base-pair change (single nucleotide polymorphism, or "SNP"), or a long one, for example, a microsatellite/simple sequence repeat ("SSR"). A "marker allele" or "marker allele form" refers to the version of the marker that is present in a particular individual. The term "marker" as used herein may refer to a cloned segment of chromosomal DNA, and may also or alternatively refer to a DNA molecule that is complementary to a cloned segment of chromosomal DNA. The term also refers to nucleic acid sequences complementary to genomic marker sequences, such as nucleic acid primers and probes.

A marker may be described, for example, as a specific polymorphic genetic element at a specific location in the genetic map of an organism. A genetic map may be a graphical representation of a genome (or a portion of a genome, such as a single chromosome) where the distances between landmarks on the chromosome are measured by the recombination frequencies between the landmarks. A genetic landmark can be any of a variety of known polymorphic markers, for example and without limitation: simple sequence repeat (SSR) markers; restriction fragment length polymorphism (RFLP) markers; and single nucleotide polymorphism (SNP) markers. As one example, SSR markers can be derived from genomic or expressed nucleic acids (e.g., expressed sequence tags (ESTs)).

Additional markers include, for example and without limitation, ESTs; amplified fragment length polymorphisms (AFLPs) (Vos et al. (1995) Nucl. Acids Res. 23:4407; Becker et al. (1995) Mol. Gen. Genet. 249:65; Meksem et al. (1995) Mol. Gen. Genet. 249:74); randomly amplified polymorphic DNA (RAPD); and isozyme markers. Isozyme markers may be employed as genetic markers, for example, to track isozyme markers or other types of markers that are linked to a particular first marker. Isozymes are multiple forms of enzymes that differ from one another with respect to amino acid sequence (and therefore with respect to their encoding nucleic acid sequences). Some isozymes are multimeric enzymes containing slightly different subunits. Other isozymes are either multimeric or monomeric, but have been cleaved from a pro-enzyme at different sites in the pro-enzyme amino acid sequence. Isozymes may be characterized and analyzed at the protein level or at the nucleic acid level. Thus, any of the nucleic acid based methods described herein can be used to analyze isozyme markers in particular examples.

"Genetic markers" include alleles that are polymorphic in a population, where the alleles of may be detected and distinguished by one or more analytic methods (e.g., RFLP analysis, AFLP analysis, isozyme marker analysis, SNP analysis, and SSR analysis). The term "genetic marker" may also refer to a genetic locus (a "marker locus") that may be used as a point of reference when identifying a genetically linked locus (e.g., a QTL). Such a marker may also be referred to as a "QTL marker." Markers corresponding to genetic polymorphisms between members of a population can be detected by methods known in the art. These include, but are not limited to, nucleic acid sequencing, hybridization methods, amplification methods (e.g., PCR-based sequence specific amplification methods), detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of randomly amplified polymorphic DNA (RAPD), detection of single nucleotide polymorphisms (SNPs), and/or detection of amplified fragment length polymorphisms (AFLPs). Thus, in certain examples of the invention, such known methods can be used to detect the SNP alleles defined herein. See, e.g., Table 3 below.

"Marker-assisted selection" (MAS) is a process by which phenotypes are selected based on marker genotypes. Marker assisted selection includes the use of marker genotypes for identifying plants for inclusion in and/or removal from a breeding program or planting.

Molecular marker technologies generally increase the efficiency of plant breeding through MAS. A molecular marker allele that demonstrates linkage disequilibrium with a desired phenotypic trait (e.g., a QTL) provides a useful tool for the selection of the desired trait in a plant population. The key components to the implementation of an MAS approach are the creation of a dense (information rich) genetic map of molecular markers in the plant germplasm; the detection of at least one QTL based on statistical associations between marker and phenotypic variability; the definition of a set of particular useful marker alleles based on the results of the QTL analysis; and the use and/or extrapolation of this information to the current set of breeding germplasm to enable marker-based selection decisions to be made.

Linkage (dis)equilibrium: As used herein, the term "linkage equilibrium" refers to the situation where two markers independently segregate; i.e., the markers sort randomly among progeny. Markers that show linkage equilibrium are considered unlinked (whether or not they lie on the same chromosome). As used herein, the term "linkage disequilibrium" refers to the situation where two markers segregate in a non-random manner; i.e., the markers have a recombination frequency of less than 50% (and thus by definition, are separated by less than 50 cM on the same linkage group). In some examples, markers that show linkage disequilibrium are considered linked.

Linked, tightly linked, and extremely tightly linked: As used herein, linkage between genes or markers may refer to the phenomenon in which genes or markers on a chromosome show a measurable probability of being passed on together to individuals in the next generation. Thus, linkage of one marker to another marker or gene may be measured and/or expressed as a recombination frequency. The closer two genes or markers are to each other, the closer to "1" this probability becomes. Thus, the term "linked" may refer to one or more genes or markers that are passed together with a gene with a probability greater than 0.5 (which is expected from independent assortment where markers/genes are located on different chromosomes). When the presence of a gene contributes to a phenotype in an individual, markers that are linked to the gene may be said to be linked to the phenotype. Thus, the term "linked" may refer to a relationship between a marker and a gene, or between a marker and a phenotype.

A relative genetic distance (determined by crossing over frequencies and measured in centimorgans (cM)) is generally proportional to the physical distance (measured in base pairs) that two linked markers or genes are separated from each other on a chromosome. One centimorgan is defined as the distance between two genetic markers that show a 1% recombination frequency (i.e., a crossing-over event occurs between the two markers once in every 100 cell divisions). In general, the closer one marker is to another marker or gene (whether the distance between them is measured in terms of genetic distance or physical distance), the more tightly they are linked. Because chromosomal distance is approximately proportional to the frequency of recombination events between traits, there is an approximate physical distance that correlates with recombination frequency. As used herein, the term "linked" may refer to one or more genes or markers that are separated by a genetic distance of less than about 50 cM. Thus, two "linked" genes or markers may be separated by less than about 45 cM; less than about 40 cM; less than about 35 cM; less than about 30 cM; less than about 25 cM; less than about 20 cM; less than about 15 cM; less than about 10 cM; and less than about 5 cM.

As used herein, the term "tightly linked" may refer to one or more genes or markers that are located within about 35 cM of one another. Thus, two "tightly linked" genes or markers may be separated by less than 36 cM; less than 35 cM; less than 34 cM; less than about 33 cM; less than about 32 cM; less than about 31 cM; less than about 30 cM; less than about 29 cM; less than about 28 cM; less than about 27 cM; less than about 26 cM; less than about 25 cM; less than about 24 cM; less than about 23 cM; less than about 22 cM; less than about 21 cM; less than about 20 cM; less than about 19 cM; less than about 18 cM; less than about 17 cM; less than about 16 cM; less than about 15 cM; less than about 14 cM; less than about 13 cM; less than about 12 cM; less than about 11 cM; less than about 10 cM; less than about 9 cM; less than about 8 cM; less than about 7 cM; less than about 6 cM; less than about 5 cM; and even smaller genetic distances.

As used herein, the term "extremely tightly-linked" may refer to one or more genes or markers that are located within about 5.0 cM of one another. Thus, two "extremely tightly-linked" genes or markers may be separated by less than 6.0 cM; less than 5.5 cM; less than 5.0 cM; less than about 4.5 cM; less than about 4.0 cM; less than about 3.5 cM; less than about 3.0 cM; less than about 2.5 cM; less than about 2.0 cM; less than about 1.5 cM; less than about 1.0 cM; and less than about 0.5 cM.

The closer a particular marker is to a gene that encodes a polypeptide that contributes to a particular phenotype (whether measured in terms of genetic or physical distance), the more tightly-linked is the particular marker to the phenotype. In view of the foregoing, it will be appreciated that markers linked to a particular gene or phenotype include those markers that are tightly linked, and those markers that are extremely tightly linked, to the gene or phenotype. In some embodiments, the closer a particular marker is to a gene that contributes to low fiber content phenotype (whether measured in terms of genetic or physical distance), the more tightly-linked is the particular marker to the low fiber content phenotype. Thus, linked, tightly linked, and extremely tightly linked genetic markers of a low fiber content phenotype in canola may be useful in MAS programs to identity canola varieties comprising low fiber content (when compared to parental varieties and/or at least one particular conventional variety), to identify individual canola plants comprising low fiber content, and to breed this trait into other canola varieties (e.g., "AC" genome, such as B. napus) to decrease fiber content. Marker set: As used herein, a "set" of markers or probes refers to a specific collection of markers (or data derived therefrom) that may be used to identify individuals comprising a trait of interest. In some embodiments, a set of markers linked to a low fiber content phenotype may be used to identify a canola plant comprising low fiber content. Data corresponding to a marker set (or data derived from the use of such markers) may be stored in an electronic medium. While each marker in a marker set may possess utility with respect to trait identification, individual markers selected from the set and subsets including some, but not all, of the markers may also be effective in identifying individuals comprising the trait of interest.

Allele: As used herein, the term "allele" refers to one of two or more different nucleotide sequences that occur at a specific locus. For example, a first allele may occur on one chromosome, while a second allele may occur on a second homologous chromosome; e.g., as occurs for different chromosomes of a heterozygous individual, or between different homozygous or heterozygous individuals in a population. In some embodiments, a particular allele at a particular locus may be linked to an agronomically desirable phenotype (e.g., low fiber content). In some embodiments, a particular allele at the locus may allow the identification of plants that do not comprise the agronomically desirable phenotype (e.g., high fiber content plants), such that those plants may be removed from a breeding program or planting. A marker allele may segregate with a favorable phenotype, therefore providing the benefit of identifying plants comprising the phenotype. An "allelic form of a chromosome segment" may refer to a chromosome segment that comprises a marker allele nucleotide sequence that contributes to, or is linked to, a particular phenotype at one or more genetic loci physically located on the chromosome segment.

Single-nucleotide polymorphism: As used herein, the term "single-nucleotide polymorphism" (SNP) may refer to a DNA sequence variation occurring when a single nucleotide in the genome (or other shared sequence) differs between members of a species or paired chromosomes in an individual. In some examples, markers linked to low fiber content are SNP markers. Recent high-throughput genotyping technologies such as GoldenGate® and INFINIUM® assays (Illumina, San Diego, Calif.) may be used in accurate and quick genotyping methods by multiplexing SNPs from 384-plex to >100,000-plex assays per sample. Other exemplary technologies for interrogating SNPs include nucleic acid sequencing (e.g., next-generation sequencing or NGS), primer extension, allele-specific PCR (e.g. KASP), H2-dependent PCR (rhPCR), Melt Analysis of Mismatch Amplification Mutation Assay (Melt-MAMA), Masscode™ (Qiagen, Germantown, Md.), Invader® (Hologic, Madison, Wis.), Serial Invasive Signal Amplification Reaction (SI-SAR), SnapShot® (Applied Biosystems, Foster City, Calif.), and Taqman® (Applied Biosystems, Foster City, Calif.). Although SNP markers are highly useful, availability of high quality DNA sequence information is necessary for their discovery.

Plant: As used herein, the term "plant" may refer to a whole plant, a cell or tissue culture derived from a plant, and/or any part of any of the foregoing. Thus, the term "plant" encompasses, for example and without limitation, whole plants; plant components and/or organs (e.g., leaves, stems, and roots); plant tissue; seed; and a plant cell. A plant cell may be, for example and without limitation, a cell in and/or of a plant, a cell isolated from a plant, and a cell obtained through culturing of a cell isolated from a plant. Thus, the term "canola plant" may refer to, for example and without limitation, a whole canola plant; multiple canola plants; canola plant cell(s); canola plant protoplast; canola tissue culture (e.g., from which a canola plant can be regenerated); canola plant callus; canola plant parts (e.g., canola seed, canola flower, canola cotyledon, canola leaf, canola stem, canola bud, canola root, and canola root tip); and canola plant cells that are intact in a canola plant or in a part of a canola plant.

Plant line: As used herein, a "line" refers to a group of plants that display little genetic variation (e.g., no genetic variation) between individuals for at least one trait. Inbred lines may be created by several generations of self-pollination and selection or, alternatively, by vegetative propagation from a single parent using tissue or cell culture techniques. As used herein, the terms "cultivar," "variety," and "type" are synonymous, and these terms refer to a line that is used for commercial production.

A "variety" or "cultivar" is a plant line that is used for commercial production which is distinct, stable and uniform in its characteristics when propagated. In the case of a hybrid variety or cultivar, the parental lines are distinct, stable, and uniform in their characteristics.

Commercially useful: As used herein, the term "commercially useful" refers to plant lines and hybrids that have sufficient plant vigor and fertility, such that a crop of the plant line or hybrid can be produced by farmers using conventional farming equipment. In particular embodiments, plant commodity products with described components and/or qualities may be extracted from plants or plant materials of the commercially useful variety. For example, oil comprising desired oil components may be extracted from the seed of a commercially useful plant line or hybrid utilizing conventional crushing and extraction equipment. In another example, enhanced canola meal (defined herein) may be prepared from the crushed seed of commercially useful plant lines which are provided by the invention and which have one or more low fiber content marker disclosed herein. In certain embodiments, a commercially useful plant line is an inbred line or a hybrid line. "Agronomically elite" lines and hybrids typically have desirable agronomic characteristics; for example and without limitation: improved yield of at least one plant commodity product; maturity; disease resistance; and standability.

Plant commodity product: As used herein, the term "plant commodity product" refers to commodities produced from a particular plant or plant part (e.g., a plant comprising a germplasm of the invention, and a plant part obtained from a plant comprising a germplasm of the invention). A commodity product may be, for example and without limitation: grain; meal; forage; protein; isolated protein; flour; oil; crushed or whole grains or seeds; any food product comprising any meal, oil, or crushed or whole grain; or silage.

Enhanced canola meal: As used herein, the term "enhanced canola meal" means canola meal, produced from canola seeds, which has decreased fiber content, and may have increased protein and true metabolizable energy content, as well as reduced anti-nutritional factors such as glucosinolates, tannins, phytic acid, sinapine and erucic acid. Meal with some or all of these characteristics could allow increasing inclusion rates in the diet of animal species especially in monogastric animals. The enhanced canola meal which of the present invention may variously be referred to herein as "ECM," "black seeded canola ECM," "BSC ECM," or "dark seeded canola ECM." The present invention is not limited to black-seeded canola and black seeded canola ECM.

Fiber is a component of plant cell walls, and includes carbohydrate polymers (e.g., cellulose (linear glucose polymeric chains)); hemicellulose (branched chains of heteropolymers of, for example, galactose, xylose, arabinose, rhamnose, with phenolic molecules attached); and pectins (water soluble polymers of galacturonic acid, xylose, arabinose, with different degrees of methylation). Fiber also includes polyphenolic polymers (e.g., lignin-like polymers and condensed tannins).

The quality of meal is measured by the percentages of Acid Detergent Fiber (ADF) and Neutral Detergent Fiber (NDF) they contain. The levels of ADF and NDF are critical because they impact animal productivity and digestion. ADF is a measure of the plant components in forages that is least digestible by livestock, including cellulose and lignin. NDF measures most of the structural components in plant cells (i.e. lignin, hemicellulose and cellulose), but not pectin. Decreased ADF and NDF also results in more digestible, higher energy meal.

In particular embodiments, a seed of a canola plant (e.g., a dark-seeded canola plant) comprising a germplasm described herein may have a decreased ADF, as compared to a reference canola variety. In certain embodiments, "high" or "low" component content refers to a comparison between a seed produced by a reference plant comprising a germplasm described herein and a seed produced by standard canola varieties. Thus, a plant producing a seed with "low" fiber content may produce a seed with a lower fiber content than is observed in a seed produced by standard canola varieties.

Trait or phenotype: The terms "trait" and "phenotype" are used interchangeably herein. For the purposes of the present disclosure, the traits of particular interest are low fiber content and, in some cases, seed coat color. Some canola varieties exhibit a yellow seed coat, while further varieties exhibit a dark (e.g., black, dark, and mottled) seed coat.

Seed color: Canola varieties (e.g., inbred canola lines and hybrids) can be characterized by seed color. Canola seed color rating or "seed color" is generally scored on a 1-5 scale, based on seeds obtained from healthy plants at or near complete seed maturity. "1" signifies a good yellow color. "2" signifies mainly yellow with some brown. "3" indicates a mixture of brown and yellow. "4" and "5" signify brown and black, respectively.

III Mapping and Validation of the Low Fiber Content Trait from CL044864 and CL065620

Genetic loci correlating with particular phenotypes, such as low fiber content, can be mapped in an organism's genome. By identifying a marker or cluster of markers that co-segregate with a trait of interest, the breeder is able to rapidly select a desired phenotype by selecting for the proper marker (a process called marker-assisted selection, or MAS). Such markers may also be used by breeders to design genotypes in silico and to practice whole genome selection.

The present invention provides a chromosomal interval and molecular markers associated with low fiber content in canola. Detection of these markers and/or other linked markers can be used to select, identify, and/or produce canola plants having low fiber content and/or to eliminate canola plants from breeding programs or from planting that do not have low fiber content.

This disclosure provides a method for identifying and mapping a quantitative trait loci (QTL) associated with a low fiber content trait in *Brassica napus* using single-nucleotide polymorphism (SNP) markers. In embodiments, the QTL is defined in BSC lines CL044864 and CL065620. In some embodiments, the markers may be used for marker-assisted selection of the low fiber content trait derived from BSC lines CL044864 and CL065620 and their lineages.

SNP markers and high-density genetic maps were leveraged, and the fiber content trait were fine mapped and validated from BSC lines CL044864 and CL065620 with an extensive set of phenotypic data from four dihaploid (DH) populations. These experiments are outlined in greater detail in Examples 1-2.

Table 3 provides the names of 92 low fiber content associated markers (SNPs) of this invention, the physical and genetic locations of each marker on canola chromosome N13, and the target allele that is associated with low fiber content. Markers of the present invention are described herein with respect to the positions of marker loci in the *B. napus* reference genome DH12075, which was sequenced at AAFC through an industry consortium.

In some examples of this invention, the markers and the marker alleles associated with low fiber content as set forth in Table 3 can be located in a chromosomal interval including, but not limited to (a) a chromosome interval on chromosome N13 defined by and including base pair (bp) position 7301735 (DBSNP143552; SEQ ID NO:1) and to base pair (bp) position 9417330 (DBSNP243314; SEQ ID NO:89); and (b) a chromosomal interval on chromosome N13 defined by and including the donor allele for each marker as set forth in Table 3. In other examples, the marker alleles associated with low fiber content include the markers set forth in Table 3 which are located on a smaller chromosome interval on *Brassica napus* chromosome N13 defined by and including bp position 8978949 (DBSNP02056, SEQ ID NO:61) to bp position 9375623 (DBSNP243323, SEQ ID NO:77). As would be understood by one of skill in the art, additional chromosomal intervals can be defined by the SNP markers provided herein in Table 3.

IV. Detection of Markers for Low Fiber Content in Canola

Embodiments of the invention include markers that are linked to low fiber content, for example, in canola derived from BSC lines CL044864 and CL065620 and their lineages. Such markers may be used, for example and without limitation, to identify canola plants and germplasm having an increased likelihood of comprising a low fiber content phenotype; to select such canola plants and germplasm (e.g., in a marker-assisted selection program); and to identify and select canola plants and germplasm that do not have an increased likelihood of comprising a low fiber content phenotype. Use of one or more of the markers describe herein may provide advantages to plant breeders with respect to the time, cost, and labor involved in canola breeding, when compared to currently available compositions and methods in the art. For example, one or more of the markers described herein may provide superior results in marker-assisted breeding of low fiber content in canola, when compared to currently available markers for this purpose.

Methods for detecting (identifying) canola plants or germplasm that carry particular alleles of low fiber content markers are a feature of some embodiments. In some embodiments, any of a variety of marker detection protocols available in the art may be used to detect a marker allele, depending on the type of marker being detected. In examples, suitable methods for marker detection may include amplification and identification of the resulting amplified marker by, for example and without limitation, PCR; LCR; and transcription-based amplification methods (e.g., SNP detection, SSR detection, RFLP analysis, and many others).

In general, a genetic marker relies on one or more property of nucleic acids for its detection. For example, some techniques for detecting genetic markers utilize hybridization of a probe nucleic acid to a nucleic acid corresponding to the genetic marker (e.g., an amplified nucleic acid produced using a genomic canola DNA molecule as a template). Hybridization formats including, for example and without limitation, solution phase; solid phase; mixed phase; and in situ hybridization assays may be useful for allele detection in particular embodiments. An extensive guide to the hybridization of nucleic acids may be found, for example, in Tijssen (1993) Laboratory Techniques in Biochemistry and Molecular Biology-Hybridization with Nucleic Acid Probes Elsevier, N.Y.

Markers corresponding to genetic polymorphisms between members of a population may be detected by any of numerous methods including, for example and without limitation, nucleic acid amplification-based methods; and nucleotide sequencing of a polymorphic marker region. Many detection methods (including amplification-based and sequencing-based methods) may be readily adapted to high throughput analysis in some examples, for example, by using available high throughput sequencing methods, such as sequencing by hybridization.

Accordingly, this invention further provides methods of identifying and/or selecting a low fiber content canola plant or germplasm, comprising: (a) detecting, in said canola plant or germplasm, the presence of one or more genetic markers associated with low fiber content in a canola plant, as described herein; and (b) selecting said canola plant or germplasm based on the presence of the one or more genetic markers associated with low fiber content in a canola plant.

Additionally, the methods of this invention include detecting an amplified DNA fragment associated with the presence of a particular allele of a SNP. In some embodiments, the amplified fragment associated with a particular allele of a SNP has a predicted nucleic acid sequence, and detecting an amplified DNA fragment having the predicted nucleic acid sequence is performed such that the amplified DNA fragment has the nucleic acid sequence that corresponds (e.g., a homology of at least about 80%, 90%, 95%, 96%, 97%, 98%, 99% or more) to the expected sequence based on the sequence of the marker associated with that SNP in the plant in which the marker was first detected.

The detecting of a particular allele of a SNP can be performed by any of a number or techniques, including, but not limited to, the use of detectable labels. Detectable labels suitable for use include any composition detectable by spectroscopic, radioisotopic, photochemical, biochemical, immunochemical, electrical, optical, or chemical means. Thus, a particular allele of a SNP may be detected using, for example, autoradiography, fluorography, or other similar detection techniques, depending on the particular label to be detected. Useful labels include biotin (for staining with labeled streptavidin conjugate), magnetic beads, fluorescent dyes, radiolabels, enzymes, and colorimetric labels. Other labels include ligands that bind to antibodies or specific binding targets labeled with fluorophores, chemiluminescent agents, and enzymes. In some embodiments of the present invention, detection techniques include the use of fluorescent dyes.

Several methods are available for SNP genotyping, including but not limited to, hybridization, primer extension, oligonucleotide ligation, nuclease cleavage, minisequencing and coded spheres. Such methods have been reviewed in various publications: Gut, Hum. Mutat. 17:475 (2001); Shi, Clin. Chem. 47:164 (2001); Kwok, Pharmacogenomics 1:95 (2000); Bhattramakki and Rafalski, Discovery and application of single nucleotide polymorphism markers in plants, in PLANT GENOTYPING: THE DNA FINGERPRINTING OF PLANTS, CABI Publishing, Wallingford (2001). A wide range of commercially available technologies utilize these and other methods to interrogate SNPs, including Masscode™ (Qiagen, Germantown, Md.), Invader® (Hologic, Madison, Wis.), SnapShot® (Applied Biosystems, Foster City, Calif.), Taqman® (Applied Biosystems, Foster City, Calif.) and Infinium Bead Chip™ (Illumina, San Diego, Calif.). In some examples of the present invention, the method of SNP genotyping includes the use of the Infinium Bead Chip™

The SNP markers of this invention and their corresponding SNP alleles are disclosed in Table 3 and are associated with low fiber content. One marker or a combination of markers can be used to detect the presence of a low fiber content plant. For example, a marker can be located within a chromosomal interval defining a QTL or be present in the genome of the plant as a haplotype as defined herein. The chromosomal interval of the present invention comprises an interval on chromosome N13 defined by and including base pair (bp) position 7301735 (DBSNP143552; SEQ ID NO:1) and to bp position 9417330 (DBSNP243314; SEQ ID NO:89). The chromosomal interval of the present invention can also be a smaller chromosome interval on chromosome N13 defined by and including bp position 8978949

(DBSNP02056, SEQ ID NO:61) to bp position 9375623 (DBSNP243323, SEQ ID NO:77).

Accordingly, in some aspects of the present invention, a method of selecting, detecting and/or identifying a low fiber content canola plant or germplasm is provided, the method comprising: detecting, in said canola plant or germplasm, the presence of a marker (e.g., a marker allele) associated with low fiber content in a canola plant, wherein said marker is located within a chromosomal interval. The chromosomal interval can comprise, consist essentially of, or consist of a chromosome interval on chromosome N13 defined by and including bp position 7301735 (DBSNP143552; SEQ ID NO:1) to bp position 9417330 (DBSNP243314; SEQ ID NO:89), thereby identifying and/or selecting a low fiber content canola plant or germplasm. Also, the chromosomal interval can comprise, consist essentially of, or consist of a chromosome interval on chromosome N13 defined by and including bp position 8978949 (DBSNP02056, SEQ ID NO:61) to bp position 9375623 (DBSNP243323, SEQ ID NO:77). In some examples, each marker described herein can be defined by a donor allele, which can be the donor allele for each marker sequence SEQ ID NO:1-89, SEQ ID NO:90, SEQ ID NO:95, and SEQ ID NO:100 is described in Table 3.

V. Introgression of Markers for Low Fiber Content into Canola

As set forth, supra, identification of canola plants or germplasm that includes a marker allele or alleles that is/are linked to a low fiber content phenotype provides a basis for performing marker assisted selection of canola. For example, at least one canola plant that comprises at least one marker allele that is positively correlated with low fiber content is selected. Canola plants that comprise marker alleles that are negatively correlated with low fiber content may be selected against.

This disclosure thus provides methods for selecting a canola plant exhibiting low fiber content comprising detecting in the plant the presence of one or more genetic markers associated with low fiber content as defined herein. The invention provides a method for selecting such a plant, the method comprises providing a sample of genomic DNA from a canola plant; and (b) detecting in the sample of genomic DNA at least one genetic marker associated with low fiber content as described herein. Detecting can comprise detecting one or more SNPs, a combination of SNPs (haplotype), and/or SNPs located in chromosomal intervals that are associated with low fiber content. In some examples of the invention, the interval is chromosome N13 defined by and including bp position 7301735 (DBSNP143552; SEQ ID NO:1) to bp position 9417330 (DBSNP243314; SEQ ID NO:89), which includes the genetic markers (SNPs) provided as SEQ ID NOs:1-89, SEQ ID NO:90, SEQ ID NO:95, and SEQ ID NO:100 having donor alleles disclosed in Table 3. In another example of the invention, the method involves detecting in the sample of genomic DNA at least one genetic marker located in the smaller N13 interval that is defined by and includes bp position 8978949 (DBSNP02056, SEQ ID NO:61) to bp position 9375623 (DBSNP243323, SEQ ID NO:77), which genetic markers (SNPs) provided as SEQ ID NOs:61, 62, 63, 64, 65, 66, 67, 68, 69, 70, 71, 72, 73, 74, 75, 76, 77, or 100 having the donor alleles disclosed in Table 3.

The invention provides a method comprising the transfer by introgression of the nucleic acid sequence from a low fiber content donor canola plant into a high fiber content recipient canola plant by crossing the plants. This transfer can be accomplished by using traditional breeding techniques. Loci associated with low fiber content are introgressed in some embodiments into commercial canola varieties using marker-assisted selection (MAS) or marker-assisted breeding (MAB). MAS and MAB involve the use of one or more of the molecular markers, identified as having a significant likelihood of co-segregation with a desired trait, and used for the identification and selection of those offspring plants that contain one or more of the genes that encode the desired trait. As disclosed herein, such identification and selection are based on the selection of one or more SNP alleles located in one of the N13 intervals disclosed herein or one or more markers associated with the SNP alleles. MAB can also be used to develop near-isogenic lines (NIL) harboring one or more low fiber content alleles of interest, allowing a more detailed study of an effect of such allele(s), and is also an effective method for development of backcross inbred line (BIL) populations. Canola plants developed according to these embodiments can in some embodiments derive a majority of their traits from the recipient plant and derive the low fiber content trait from the donor plant. MAB/MAS techniques increase the efficiency of backcrossing and introgressing genes using marker-assisted selection (MAS) or marker-assisted breeding (MAB).

Thus, traditional breeding techniques can be used to introgress a nucleic acid sequence associated with low fiber content into a high fiber content recipient canola plant. For example, inbred low fiber content canola plant lines can be developed using the techniques of recurrent selection and backcrossing, selfing, and/or dihaploids, or any other technique used to make parental lines. In a method of recurrent selection and backcrossing, low fiber content can be introgressed into a target recipient plant (the recurrent parent) by crossing the recurrent parent with a first donor plant, which differs from the recurrent parent and is referred to herein as the "non-recurrent parent." The recurrent parent is a plant that has high fiber content and, in some cases, comprises commercially desirable characteristics, such as, but not limited to disease and/or insect resistance, valuable nutritional characteristics, valuable abiotic stress tolerance (including, but not limited to, drought tolerance, salt tolerance), and the like. In some cases, the non-recurrent parent exhibits low fiber content and comprises a nucleic acid sequence that is associated with low fiber content. The non-recurrent parent can be any plant variety or inbred line that is cross-fertile with the recurrent parent.

In certain examples of the disclosed introgression method, the progeny resulting from a cross between the recurrent parent and non-recurrent parent are backcrossed to the recurrent parent. The resulting plant population is then screened for the desired characteristics, which screening can occur in a number of different ways. For instance, the population can be screened using phenotypic pathology screens or quantitative bioassays as are known in the art. Alternatively, instead of using bioassays, MAB can be performed using one or more of the herein before described molecular markers to identify those progeny that comprise a nucleic acid sequence associated with low fiber content. Also, MAB can be used to confirm the results obtained from the quantitative bioassays. In some embodiments, the markers defined herein are suitable to select proper offspring plants by genotypic screening.

Following screening, the F1 hybrid plants that exhibit a low fiber content phenotype or, in some embodiments, the genotype, and thus comprise the requisite nucleic acid sequence associated with low fiber content, can then be selected and backcrossed to the recurrent parent for one or more generations in order to allow for the canola plant to become increasingly inbred. This process can be performed for one, two, three, four, five, six, seven, eight, or more generations.

Accordingly, the markers of the present invention can be used in MAS methods to identify and/or select and/or produce progeny having a genetic marker associated with low fiber content. Therefore, the present invention provides a method of selecting a low fiber content canola plant, the method comprising: detecting, in a canola germplasm, the presence of a marker associated with low fiber content in a canola plant, wherein said marker is located within a chromosomal interval disclosed herein, and selecting a plant from said germplasm, thereby selecting a low fiber canola plant. The disclosed chromosomal interval can be the N13 interval defined by and including bp position 7301735 (DBSNP143552; SEQ ID NO:1) to bp position 9417330 (DBSNP243314; SEQ ID NO:89), which includes the genetic markers (SNPs) provided as SEQ ID NOs:1-89, SEQ ID NO:90, SEQ ID NO:95, and SEQ ID NO:100 having donor alleles disclosed in Table 3. The method disclosed interval can also be the N13 interval defined by and including bp position 8978949 (DBSNP02056, SEQ ID NO:61) to bp position 9375623 (DBSNP243323, SEQ ID NO:77), which genetic markers (SNPs) provided as SEQ ID NOs:61, 62, 63, 64, 65, 66, 67, 68, 69, 70, 71, 72, 73, 74, 75, 76, 77, or 100 having the donor alleles disclosed in Table 3.

The invention also provides a method of producing a low fiber content plant and/or germplasm is provided, the method comprising: crossing a first canola plant or germplasm with a second canola plant or germplasm, wherein said first canola plant or germplasm comprises within its genome a marker associated with low fiber content in a canola plant, wherein said marker is located within a chromosomal interval disclosed herein, collecting seed from the cross and growing a progeny canola plant from the seed, wherein said progeny canola plant comprises in its genome said marker associated with low fiber content, thereby producing a low fiber content canola plant. The disclosed chromosomal interval can be the N13 interval defined by and including bp position 7301735 (DBSNP143552; SEQ ID NO:1) to bp position 9417330 (DBSNP243314; SEQ ID NO:89), which includes the genetic markers (SNPs) provided as SEQ ID NOs:1-89, SEQ ID NO:90, SEQ ID NO:95, and SEQ ID NO:100 having donor alleles disclosed in Table 3. The method disclosed interval can also be the N13 interval defined by and including bp position 8978949 (DBSNP02056, SEQ ID NO:61) to bp position 9375623 (DBSNP243323, SEQ ID NO:77), which genetic markers (SNPs) provided as SEQ ID NOs:61, 62, 63, 64, 65, 66, 67, 68, 69, 70, 71, 72, 73, 74, 75, 76, 77, or 100 having the donor alleles disclosed in Table 3

In some examples, the second canola plant or germplasm used in the method of this invention is of an elite variety of canola. In some examples, the crossing of the first and second canola plants produces a progeny canola plant or germplasm having the low fiber content marker introgressed into a genome that is at least about 50%, 55%, 60%, 65%, 70%, 75%, 80%, 85%, 90%, 95%, 97%, 99% identical to that of an elite variety of canola.

The disclosed method can be used to introgress a genetic marker associated with low fiber content disclosed herein into a genetic background lacking said marker, the method comprising: crossing a donor comprising said marker with a recurrent parent that lacks said marker; and backcrossing progeny comprising said marker with the recurrent parent, wherein said progeny are identified by detecting in their genome the presence of a marker associated with low fiber content in a canola plant. Said marker is located within a chromosome interval on chromosome N13 defined by and including marker DBSNP143552 (SEQ ID NO:1) at 7301735 bp to marker DBSNP243314 (SEQ ID NO:89) at 9417330 bp. In some examples, said marker is located on the N13 interval defined by and including bp position 8978949 (DBSNP02056, SEQ ID NO:61) to bp position 9375623 (DBSNP243323, SEQ ID NO:77). Donor alleles of said markers are identified in Table 3. The method produces a low fiber content canola plant or germplasm comprising said genetic marker associated with low fiber content in the genetic background of the recurrent parent, thereby introgressing the genetic marker associated with low fiber content into a genetic background lacking said marker.

The present invention provides canola plants and germplasms having low fiber content. As discussed above, the methods of the present invention can be utilized to identify, select and/or produce a canola plant or germplasm having low fiber content. In addition to the methods described above, a canola plant or germplasm having low fiber content may be produced by any method whereby a marker associated with low fiber content in a canola plant is introduced into the canola plant or germplasm by such methods that include, but are not limited to, transformation (including, but not limited to, bacterial-mediated nucleic acid delivery (e.g., via Agrobacteria)), viral-mediated nucleic acid delivery, silicon carbide or nucleic acid whisker-mediated nucleic acid delivery, liposome mediated nucleic acid delivery, microinjection, microparticle bombardment, electroporation, sonication, infiltration, PEG-mediated nucleic acid uptake, as well as any other electrical, chemical, physical (mechanical) and/or biological mechanism that results in the introduction of nucleic acid into the plant cell, or any combination thereof, protoplast transformation or fusion, a double haploid technique, embryo rescue, or by any other nucleic acid transfer system.

"Introducing" in the context of a plant cell, plant and/or plant part means contacting a nucleic acid molecule with the plant, plant part, and/or plant cell in such a manner that the nucleic acid molecule gains access to the interior of the plant cell and/or a cell of the plant and/or plant part. Where more than one nucleic acid molecule is to be introduced, these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell.

Thus, a canola plant, or part thereof, having a genetic marker associated with low fiber content, obtainable by the methods of the presently disclosed subject matter, are aspects of the presently disclosed subject matter.

The canola plant or germplasm may be the progeny of a cross between an elite variety of canola and a variety of canola that comprises an allele associated with low fiber content. In some embodiments, the canola plant or germplasm is at least about 50%, 55%, 60%, 65%, 70%, 75%, 80%, 85%, 90%, 95%, 97%, 99% or 100% identical to that of an elite variety of canola.

The canola plant or germplasm may be the progeny of an introgression wherein the recurrent parent is an elite variety of canola and the donor comprises a genetic marker associated (e.g., SNP, combination of SNPs, SNP located in a chromosome interval) with low fiber content in a canola plant as described herein.

The canola plant or germplasm may be the progeny of a cross between a first elite variety of canola (e.g., a tester line) and the progeny of a cross between a second elite variety of canola (e.g., a recurrent parent) and a variety of canola that comprises a genetic marker associated with low fiber content in a canola plant as described herein (e.g., a donor).

Another aspect of the presently disclosed subject matter relates to a method of producing seeds that can be grown into low fiber content canola plants. In some embodiments, the method comprises providing a low fiber content canola plant of this invention, crossing the low fiber content canola plant with another canola plant, and collecting seeds resulting from the cross, which when planted, produce low fiber content canola plants.

Accordingly, the present invention provides improved canola plants, seeds, and/or canola tissue culture produced by the methods described herein.

In some embodiments, the presently disclosed subject matter provides methods for analyzing the genomes of canola plants/germplasms to identify those that include desired markers associated with low fiber content. In some embodiments, the methods of analysis comprise amplifying subsequences of the genomes of the canola plants/germplasms and determining the nucleotides present in one, some, or all positions of the amplified subsequences.

Thus, the present invention provides methods for detecting alleles associated with low fiber content in canola. In some examples, allele discrimination is performed in a microtiter plate using Infinium Bead Chip™ technology and GoldenGate™ allele-specific extension PCR-based assay (Illumina, San Diego, Calif.), which identifies each SNP with a discrete fluorescent tag and a unique address to target a particular bead in the array. In further embodiments, the reaction products or fluorescent intensities on the beads are captured and the SNP allele associated with low fiber content in canola is determined. In some embodiments, the canola SNP alleles correspond to the canola SNP markers comprising a nucleotide sequence of any of SEQ ID NOs: 1-89, SEQ ID NO:90, SEQ ID NO:95, and SEQ ID NO:100.

All references, including publications, patents, and patent applications, cited herein are hereby incorporated by reference to the extent they are not inconsistent with the explicit details of this disclosure, and so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

The following examples are included to demonstrate various embodiments of the invention and are not intended to be a detailed catalog of all the different ways in which the present invention may be implemented or of all the features that may be added to the present invention. Persons skilled in the art will appreciate that numerous variations and additions to the various embodiments may be made without departing from the present invention. Hence, the following descriptions are intended to illustrate some particular embodiments of the invention, and not to exhaustively specify all permutations, combinations and variations thereof.

EXAMPLES

Example 1: Plant Materials

Two DH populations, PG803 and PG818, were developed from spring canola line crosses to identify and confirm the low fiber content QTL. The 363 DH lines of the PG803 population were developed from a cross between the black-seeded/high fiber reference line DH12075 and NEXERA black seeded/low fiber variety CL044864. The 367 DH lines of the PG818 population were developed from a cross between two black-seeded/low fiber NEXERA lines, CL044864 and CL065620 to confirm that the two BSC lines have the same low fiber content QTL on N13. Another two populations, PG856 and PG872, were also developed by crossing the Agriculture and Agri-Food Canada (AAFC) yellow-seeded, low fiber line YN01-429 with CL044864 and CL065620, respectively, to validate and confirm that the low fiber content QTL found in CL044864 and CL065620 is different from the low fiber content QTL found in YSC YN01-429. Mapping populations used in this study, their purpose and results are described in Table 1 (BSC=black seed coat; YSC=yellow seed coat; HFC=high fiber content; LFC=low fiber content QTL=quantitative trait loci).

TABLE 1

| Pop | Female Parent | Male Parent | Population Size | Number Markers Mapped | Purpose | Result |
|---|---|---|---|---|---|---|
| PG803 | DH12075 (BSC/HFC) | CL044864 (BSC/LFC) | 363 (DH) | 16,216 | Mapping of LFC trait from BSC line CL044864 | Identified a LFC QTL from BSC line CL044864 and fine mapped to a 6.2 cM region on N13 |
| PG818 | CL044864 (BSC/LFC) | CL065620 (BSC/LFC) | 367 (DH) | 1,427 | Allelism examination and interaction between the two BSC sources of LFC trait | Confirmed that CL044864 and CL065620 had the same LFC QTL on N13. |
| PG856 | YN01-429 (YSC/LFC) | CL044864 (BSC/LFC) | 403 (DH) | 3,003 | QTL validation. Allelism examination and interaction between the BSC and YSC | Validated and confirmed the LFC QTL from BSC line CL044864 and YSC line |

TABLE 1-continued

| Pop | Female Parent | Male Parent | Population Size | Number Markers Mapped | Purpose | Result |
|---|---|---|---|---|---|---|
| | | | | | sources of LFC trait. | YN01-429 were different. Either the BSC or the YSC QTL is sufficient to result in the LFC trait. |
| PG872 | CL065620 (BSC/LFC) | YN01-429 (YSC/LFC) | 392 (DH) | 2,529 | QTL validation. Allelism examination and interaction between the BSC and YSC sources of LFC trait. | Confirm the LFC QTL from YN01-429 on N09 and the LFC QTL from CL065620 on N13. |
| PG2015-1278 | DH12075 | CL044864 | 395 (F2) | 981 | Recombinant Selection for N13 Fine Mapping | Recombinants selected for further propagation. |
| PG2017-1514 | DH12075/ CL044864 | DH12075/ CL044864 | 2845 (F2:F3) | 48 | Fine Mapping of N13 Locus for Low Fiber Content | Narrowed down N13 Locus to an approximate 400 kB region. |

All of the DH lines from the four populations were grown under field conditions at Pike Lake in Saskatchewan, Canada during the 2013 and 2014 field seasons. All of the DH lines were planted in a non-replicated nursery format where each line had a 2-row single plot. DH lines were grown and harvested using standard agronomic practices.

Example 2: Phenotypic, Genotypic Data, and Linkage Map Construction and QTL Mapping The bulk seed collected for each DH line was cleaned and subjected to chemical analysis to determine ADF content using the AOAC reference method (AOAC Official Method 973.18). Two years of phenotypic data were collected in 2013 and 2014. Genomic DNA for the four populations described in Table 1 was extracted. The DH lines developed from all four populations were genotyped with a 60K SNP Illumina Infinium® Bead Chip on the BeadStation 500 G per manufacturer's protocol (Illumina, San Diego, Calif.).

Individual maps for the four DH populations, PG803, PG818, PG856 and PG872 were constructed with MAP-MAKER/EXP 3.0 (Lander et al. 1987; Lincoln et al. 1992) at LOD score 10.0 and Haldane's mapping function. A consensus map was constructed with Phenomap Enterprise 3.0 (GeneFlow Inc., Centreville, Va.). A total of 16216 SNP markers were mapped. Composite Interval Mapping (CIM), as implemented in QTL Cartographer V2.5 (Wang et al. 2011), was used for QTL mapping. A LOD score of 3.0 was used as threshold to identify genomic regions significantly affecting the acid detergent fiber content trait.

The map for the PG803 (CL044864) population was constructed with 363 DH lines and 16,216 SNP markers. A single major QTL explaining 71.5% (2013) and 65.9% (2014) of the phenotypic variation for % ADF was detected on chromosome N13. This locus represents a QTL for low fiber content from the BSC line CL044864.

The map for the PG818 (CL044864×CL065620) population was constructed with 367 DH lines and 1427 SNP markers. Table 2 shows exemplary markers produced by QTL mapping in PG818: CL044864×CL065620 for allele examination and interaction of two LFC trait QTL. A single major QTL for low fiber content was detected on chromosome N13 in the same region as identified in the PG803 population. Two years of QTL mapping data confirmed that the BSC lines CL044864 and CL065620 had the same low fiber content QTL on N13.

Populations PG856 (YN01-429×CL044864) and PG872 (CL065620×YN01-429) were used to study the interaction between the YSC N09 low fiber content QTL from YN01-429 and the BSC N13 low fiber content QTL from CL044864 and CL065620 and to further validate the BSC N13 QTL. The map for the PG856 population was constructed with 403 DH lines and 3,003 SNP markers. The map for the PG872 population was constructed with 392 DH lines and 2,529 SNP markers. The two QTL were confirmed on N09 for YSC and N13 for BSC. 92 SNP markers were mapped to a 6.2 cM region around the low fiber content QTL on chromosome N13 as shown in FIG. 1 and Table 3.

This example demonstrates the use of SNP markers and proprietary high-density genetic maps to map and validate the low ADF content from NEXERA BSC lines CL044864 and CL065620, using two years of phenotypic data from four different DH populations. A major QTL, which explained ~70% of the variance for ADF, was identified on chromosome N13 and was validated in two different populations. The markers within this interval around major QTL for ADF content may be used for MAS in canola breeding.

Additional fine mapping narrowed the QTL interval on N13 to an approximately 400 kb region flanked by and including SNP markers DBSNP02056 (SEQ ID NO:61) and DBSNP243323 (SEQ ID NO:77).

TABLE 2

| Chrom | Genetic Distance (cM) | # of Markers | Density | Coverage |
|---|---|---|---|---|
| N01 | 4.0 | 9 | 0.50 | 0.02 |
| N02 | 73.1 | 96 | 0.77 | 0.89 |
| N03 | 132.5 | 180 | 0.74 | 0.77 |
| N04 | 50.0 | 23 | 2.27 | 0.97 |

TABLE 2-continued

| Chrom | Genetic Distance (cM) | # of Markers | Density | Coverage |
|---|---|---|---|---|
| N05 | 12.0 | 17 | 0.75 | 0.04 |
| N06 | 57.9 | 79 | 0.74 | 0.61 |
| N07 | 85.4 | 171 | 0.50 | 0.99 |
| N08 | 23.0 | 24 | 1.00 | 0.60 |
| N09 | 106.4 | 71 | 1.52 | 0.84 |
| N10 | 54.9 | 17 | 3.43 | 0.43 |
| N11 | 80.0 | 102 | 0.79 | 0.83 |
| N12 | 44.3 | 88 | 0.51 | 0.54 |
| N13 | 146.9 | 120 | 1.23 | 0.98 |

TABLE 2-continued

| Chrom | Genetic Distance (cM) | # of Markers | Density | Coverage |
|---|---|---|---|---|
| N14 | 74.0 | 31 | 2.47 | 0.96 |
| N15 | 18.3 | 20 | 0.96 | 0.07 |
| N16 | 75.8 | 159 | 0.48 | 0.74 |
| N17 | 30.5 | 8 | 4.36 | 0.13 |
| N18 | 109.9 | 135 | 0.82 | 0.94 |
| N19 | 121.1 | 77 | 1.59 | 0.99 |
| Total | 1300.0 | 1427 | 0.92 | 0.68 |

TABLE 3

| SEQ ID NO: | SNP Name | Map Position (cM) | SNP Forward | Donor Allele | Physical distance on DH12075 reference map |
|---|---|---|---|---|---|
| 1 | DBSNP143552 | 32.4 | [A/G] | A | N13:7301735 . . . 7302454 |
| 2 | DBSNP251670 | 32.7 | [A/C] | A | N13:7316677 . . . 7316877 |
| 3 | DBSNP251668 | 33.2 | [T/C] | C | N13:7321551 . . . 7321669 |
| 4 | BN_N13_7417614 | 33.8 | [G/T] | T | N13:7417464 . . . 7417765 |
| 5 | BN_N13_7425239 | 33.8 | [A/C] | C | N13:7425089 . . . 7425389 |
| 6 | BN_N13_7444161 | 33.8 | [G/A] | A | N13:7444061 . . . 7444232 |
| 7 | BN_N13_7444297 | 33.8 | [A/C] | C | N13:7444212 . . . 7444364 |
| 8 | DBSNP229192 | 34.1 | [A/C] | C | N13:7478063 . . . 7478364 |
| 9 | DBSNP00916 | 34.3 | [C/G] | G | N13:7575499 . . . 7576632 |
| 10 | BN_N13_7600067 | 34.3 | [A/G] | G | N13:7599917 . . . 7600217 |
| 11 | BN_N13_7612265 | 34.9 | [A/G] | G | N13:7612115 . . . 7612415 |
| 12 | DBSNP153623 | 34.9 | [T/C] | T | N13:7623876 . . . 7624441 |
| 13 | BN_N13_7741311 | 35.2 | [T/C] | C | N13:7741161 . . . 7741461 |
| 14 | BN_N13_7751728 | 35.2 | [T/C] | C | N13:7751578 . . . 7751878 |
| 15 | BN_N13_7793316 | 35.2 | [A/G] | G | N13:7793166 . . . 7793466 |
| 16 | BN_N13_7793323 | 35.2 | [A/T] | T | N13:7793173 . . . 7793473 |
| 17 | DBSNP105065 | 35.5 | [T/C] | C | N13:7856559 . . . 7857277 |
| 18 | DBSNP106640 | 36.6 | [T/C] | T | N13:8233323 . . . 8234075 |
| 19 | DBSNP243494 | 36.8 | [A/G] | A | N13:8256200 . . . 8256318 |
| 20 | BN_N13_8260263 | 36.8 | [A/G] | G | N13:8260113 . . . 8260413 |
| 21 | DBSNP08830 | 36.8 | [T/G] | T | N13:8262111 . . . 8262320 |
| 22 | DBSNP243489 | 36.8 | [A/G] | G | N13:8262292 . . . 8262408 |
| 23 | BN_N13_8262719 | 36.8 | [T/A] | A | N13:8262569 . . . 8262869 |
| 24 | BN_N13_8262755 | 36.8 | [C/T] | T | N13:8262605 . . . 8362905 |
| 25 | BN_N13_8262822 | 36.8 | [G/T] | T | N13:8262672 . . . 8262972 |
| 26 | BN_N13_8264765 | 36.8 | [T/C] | C | N13:8264615 . . . 8264915 |
| 27 | BN_N13_8271530 | 36.8 | [C/G] | G | N13:8271380 . . . 8271680 |
| 28 | BN_N13_8271544 | 36.8 | [T/C] | C | N13:8271394 . . . 8271649 |
| 29 | BN_N13_8271575 | 36.8 | [G/A] | A | N13:8271425 . . . 8271725 |
| 95 | n13_59498877 | 36.8 | [G/T] | T | N13:8275781 . . . 8276181 |
| 30 | DBSNP243485 | 36.8 | [A/G] | A | N13:8300501 . . . 8300621 |
| 31 | DBSNP243479 | 37.1 | [A/G] | A | N13:8365919 . . . 8366215 |
| 32 | DBSNP03099 | 37.1 | [T/C] | C | N13:8440074 . . . 8440543 |
| 33 | DBSNP243444 | 37.1 | [T/C] | T | N13:8654910 . . . 8655030 |
| 34 | DBSNP243439 | 37.7 | [T/C] | C | N13:8747789 . . . 8748089 |
| 35 | DBSNP25950 | 38.1 | [A/T] | A | N13:8845683 . . . 8845980 |
| 36 | DBSNP243419 | 38.1 | [T/C] | C | N13:8865083 . . . 8865203 |
| 37 | DBSNP243415 | 38.1 | [T/C] | T | N13:8877820 . . . 8877939 |
| 38 | DBSNP243386 | 38.1 | [T/G] | T | N13:8900069 . . . 8900190 |
| 39 | DBSNP243385 | 38.1 | [A/G] | A | N13:8900956 . . . 8901076 |
| 40 | DBSNP243383 | 38.1 | [T/C] | T | N13:8901534 . . . 8901657 |
| 41 | BN_N13_8902116 | 38.1 | [T/C] | C | N13:8901966 . . . 8902266 |
| 42 | BN_N13_8906796 | 38.1 | [A/G] | A | N13:8906646 . . . 8906946 |
| 43 | BN_N13_8908503 | 38.1 | [A/T] | T | N13:8908353 . . . 8908653 |
| 44 | BN_N13_8908557 | 38.1 | [A/T] | T | N13:8908407 . . . 8908707 |
| 45 | BN_N13_8922223 | 38.1 | [T/C] | T | N13:8922073 . . . 8922373 |

TABLE 3-continued

| SEQ ID NO: | SNP Name | Map Position (cM) | SNP Forward | Donor Allele | Physical distance on DH12075 reference map |
|---|---|---|---|---|---|
| 46 | BN_N13_8933300 | 38.1 | [A/G] | G | N13:8933150 . . . 8933450 |
| 47 | DBSNP243381 | 38.1 | [A/G] | G | N13:8936136 . . . 8936256 |
| 48 | BN_N13_8956349 | 38.1 | [A/G] | A | N13:8956199 . . . 8956499 |
| 49 | BN_N13_8956369 | 38.1 | [C/G] | G | N13:8956219 . . . 8956519 |
| 50 | BN_N13_8956470 | 38.1 | [A/G] | G | N13:8956320 . . . 8956620 |
| 51 | BN_N13_8956480 | 38.1 | [T/C] | T | N13:8956330 . . . 8956630 |
| 52 | DBSNP243379 | 38.1 | [A/G] | G | N13:8956767 . . . 8956887 |
| 53 | DBSNP243378 | 38.1 | [T/C] | T | N13:8961669 . . . 8961790 |
| 54 | DBSNP324221 | 38.1 | [T/G] | T | N13:8962358 . . . 8963294 |
| 55 | BN_N13_8965169 | 38.1 | [G/C] | C | N13:8965019 . . . 8965319 |
| 56 | DBSNP243377 | 38.1 | [A/C] | C | N13:8965871 . . . 8965991 |
| 57 | DBSNP243376 | 38.1 | [T/G] | T | N13:8970906 . . . 8971026 |
| 58 | DBSNP243374 | 38.1 | [T/C] | T | N13:8971421 . . . 8971541 |
| 59 | BN_N13_8976803 | 38.1 | [A/T] | A | N13:8976653 . . . 8976953 |
| 60 | DBSNP243372 | 38.1 | [T/C] | C | N13:8977625 . . . 8977777 |
| 61 | DBSNP02056 | 38.1 | [T/C] | T | N13:8978949 . . . 8979328 |
| 62 | DBSNP90385 | 38.4 | [A/T] | T | N13:9018526 . . . 9018974 |
| 63 | DBSNP204410 | 38.4 | [T/C] | T | N13:9028926 . . . 9029213 |
| 64 | DBSNP243362 | 38.4 | [T/G] | G | N13:9029169 . . . 9029469 |
| 65 | BN_N13_9045055 | 38.4 | [G/A] | A | N13:9044905 . . . 9045205 |
| 66 | BN_N13_9054936 | 38.4 | [A/G] | G | N13:9054786 . . . 9055086 |
| 67 | DBSNP243360 | 38.4 | [T/G] | G | N13:9055229 . . . 9055429 |
| 68 | BN_N13_9055540 | 38.4 | [A/C] | C | N13:9055390 . . . 9055690 |
| 69 | BN_N13_9057319 | 38.4 | [A/G] | A | N13:9057169 . . . 9057469 |
| 70 | BN_N13_9057331 | 38.4 | [A/G] | G | N13:9057181 . . . 9057481 |
| 100 | DBSNP53263 | 38.5 | [A/C] | C | N13:9086988 . . . 9087562 |
| 71 | BN_N13_9089148 | 38.5 | [T/G] | T | N13:9088998 . . . 9089298 |
| 72 | BN_N13_9089216 | 38.5 | [C/G] | G | N13:9089066 . . . 9089366 |
| 73 | BN_N13_9091158 | 38.5 | [A/C] | A | N13:9091008 . . . 9091308 |
| 74 | BN_N13_9095137 | 38.5 | [A/T] | T | N13:9094987 . . . 9095287 |
| 75 | BN_N13_9123132 | 38.5 | [A/G] | G | N13:9122982 . . . 9123282 |
| 76 | BN_N13_9189237 | 38.5 | [G/T] | G | N13:9189087 . . . 9189278 |
| 77 | DBSNP243323 | 38.6 | [T/C] | C | N13:9375506 . . . 9375623 |
| 78 | DBSNP243322 | 38.6 | [A/G] | G | N13:9375578 . . . 9375698 |
| 79 | BN_N13_9376703 | 38.6 | [A/G] | A | N13:9376553 . . . 9376853 |
| 80 | BN_N13_9378935 | 38.6 | [T/G] | G | N13:9378785 . . . 9379085 |
| 81 | DBSNP243321 | 38.6 | [A/C] | C | N13:9379162 . . . 9379281 |
| 82 | DBSNP243319 | 38.6 | [A/C] | A | N13:9379565 . . . 9379685 |
| 83 | DBSNP243318 | 38.6 | [T/C] | T | N13:9379638 . . . 9379758 |
| 90 | n13:58387757 | 38.6 | [C/T] | T | N13:9386901 . . . 9387301 |
| 84 | BN_N13_9388558 | 38.6 | [C/G] | G | N13:9388408 . . . 9388708 |
| 85 | DBSNP243317 | 38.6 | [A/G] | A | N13:9389728 . . . 9389846 |
| 86 | DBSNP243316 | 38.6 | [A/G] | G | N13:9414794 . . . 9414914 |
| 87 | DBSNP38517 | 38.6 | [T/C] | T | N13:9416209 . . . 9417209 |
| 88 | DBSNP243315 | 38.6 | [T/C] | T | N13:9416609 . . . 9416809 |
| 89 | DBSNP243314 | 38.6 | [A/T] | A | N13:9417130 . . . 9417330 |

Example 3: TAQMAN™ Assays

TAQMAN™ assays were designed for two SNPs that are highly specific to the donor in the targeted area: SNP markers n13:58387757 (SEQ ID NO:90) and n13_59498877 (SEQ ID NO:95). TAQMAN™ primers and probes for both assays are listed in Table 4. 1.5 ul of the ~6 ng/µ.1 DNA was used in the assay mix. 18 µM of each probe, and 4 µM of each primer was combined to make each assay. 13.6 µl of the assay was combined with 1000 µl of TOUGHMIX master mix (Quanta Beverly, Mass., USA). A MERIDIAN liquid handler (LGC Genomics, Hoddesdon, Hertfordshire, UK)

dispensed 1.3 µl of the mix onto a 1536 plate containing ~6 ng of dried DNA. The plate was sealed with a Phusion laser sealer (LGC Genomics, Hoddesdon, Hertfordshire, UK) and thermocycled using a hydrocycler (from LGC Genomics) with the following conditions: 94° C. for 15 min, 40 cycles of 94° C. for 30 secs, 60° C. for 1 min. PCR products were measured at wavelengths 485 (FAM) and 520 (VIC) using a Pherastar plate reader (BMG Labtech, Offenburg, Germany). The values were normalized against ROX and plotted and scored on scatterplots utilizing the KRAKEN software (LGC Genomics, Hoddesdon, Hertfordshire, UK). Genotype was determined by the presence or absence of fluorescence specific to the SNP that was assayed.

TABLE 4

| SNP Name | Sequence | Function | SEQ ID NO: |
|---|---|---|---|
| n13:58387757 | CCAAATGAGATTTTC | FAM probe | 91 |
| | CCAAATGAAATTTTC | VIC probe | 92 |
| | TCTAAAGAAACTATGCAATGTTGTAGAGACAAA | Forward primer | 93 |
| | CACAGTTTTTGCTATCTGAGATGTTGT | Reverse primer | 94 |

TABLE 4-continued

| SNP Name | Sequence | Function | SEQ ID NO: |
|---|---|---|---|
| n13_59498877 | ATGAGAGCATTCATATTT | FAM probe | 96 |
| | TGAGAGCATGCATATTT | VIC probe | 97 |
| | GCAACATAACTAACAAGTTAAACTCCAATATTCA | Forward primer | 98 |
| | ACGCAACAAAAGCAACGATTAATCA | Reverse primer | 99 |

The invention claimed is:

1. A method for identifying a *Brassica napus* plant or germplasm that comprises a low fiber content trait, the method comprising:

a. obtaining a nucleic acid sample from a *Brassica napus* plant or germplasm;

b. screening the sample for a nucleic acid comprising one or more low fiber content marker alleles located within *Brassica napus* chromosome N13 interval between marker DBSNP143552 in SEQ ID NO:1 and marker DBSNP243314 in SEQ ID NO: 89, wherein the one or more detected marker alleles comprise one or more of an A at position 220 of SEQ ID NO:1, A at position 101 of SEQ ID NO:2, C at position 61 of SEQ ID NO:3, T at position 151 of SEQ ID NO:4, C at position 151 of SEQ ID NO:5, A at position of 101 of SEQ ID NO:6, C at position 86 of SEQ ID NO:7, C at position 151 of SEQ ID NO:8, G at position 151 of SEQ ID NO:9, G at position 151 of SEQ ID NO:10, G at position 151 of SEQ ID NO:11, T at position 150 of SEQ ID NO:12, C at position 151 of SEQ ID NO:13, C at position 151 of SEQ ID NO:14, G at position 151 of SEQ ID NO: 15, T at position 151 of SEQ ID NO:16, C at position 219 of SEQ ID NO:17, T at position 250 of SEQ ID NO:18, A at position 61 of SEQ ID NO:19, G at position 151 of SEQ ID NO:20, T at position 197 of SEQ ID NO:21, G at position 61 of SEQ ID NO:22, A at position 151 of SEQ ID NO:23, T at position 151 of SEQ ID NO:24, T at position 151 of SEQ ID NO:25, C at position 151 of SEQ ID NO:26, G at position 151 of SEQ ID NO:27, C at position 151 of SEQ ID NO:28, A at position 151 of SEQ ID NO:29, G at position 61 of SEQ ID NO:30, A at position 151 of SEQ ID NO:31, C at position 380 of SEQ ID NO:32, T at position 61 of SEQ ID NO:33, C at position 151 of SEQ ID NO:34, A at position 53 of SEQ ID NO:35, C at position 61 of SEQ ID NO:36, T at position 61 of SEQ ID NO:37, T at position 61 of SEQ ID NO:38, A at position 61 of SEQ ID NO:39, T at position 61 of SEQ ID NO:40, C at position 151 of SEQ ID NO:41, A at position 151 of SEQ ID NO:42, T at position 151 of SEQ ID NO:43, T at position 151 of SEQ ID NO:44, T at position 151 of SEQ ID NO:45, G at position 151 of SEQ ID NO:46, G at position 61 of SEQ ID NO:47, A at position 151 of SEQ ID NO:48, G at position 151 of SEQ ID NO:49, G at position 151 of SEQ ID NO:50, T at position 151 of SEQ ID NO:51, G at position 61 of SEQ ID NO:52, T at position 61 of SEQ ID NO:53, T at position 424 of SEQ ID NO:54, C at position 151 of SEQ ID NO:55, C at position 61 of SEQ ID NO:56, T at position 61 of SEQ ID NO:57, T at position 61 of SEQ ID NO:58, A at position 151 of SEQ ID NO:59, C at position 101 of SEQ ID NO:60, T at position 301 of SEQ ID NO:61, T at position 370 of SEQ ID NO:62, T at position 151 of SEQ ID NO:63, G at position 151 of SEQ ID NO:64, A at position 151 of SEQ ID NO:65, G at position 151 of SEQ ID NO:66, G at position 101 of SEQ ID NO:67, C at position 151 of SEQ ID NO:68, A at position 151 of SEQ ID NO:69, G at position 151 of SEQ ID NO:70, T at position 151 of SEQ ID NO:71, G at position 151 of SEQ ID NO: 72, A at position 151 of SEQ ID NO:73, T at position 151 of SEQ ID NO:74, G at position 151 of SEQ ID NO:75, G at position 151 of SEQ ID NO:76, C at position 61 of SEQ ID NO:77, G at position 61 of SEQ ID NO:78, A at position 151 of SEQ ID NO:79, G at position 151 of SEQ ID NO:80, C at position 61 of SEQ ID NO:81, A at position 61 of SEQ ID NO:82, T at position 61 of SEQ ID NO:83, G at position 151 of SEQ ID NO:84, A at position 61 of SEQ ID NO:85, G at position 61 of SEQ ID NO:86, T at position 501 OF SEQ ID NO:87, T at position 101 of SEQ ID NO:88, A at position 101 of SEQ ID NO:89, T at position 101 of SEQ ID NO:90, T at position 201 of SEQ ID NO:95, or C at position 90 of SEQ ID NO:100.

2. The method of claim 1, wherein the method comprises screening for and detecting the presence of one or more low fiber content marker alleles located within *Brassica napus* chromosome N13 interval between marker DBSNP02056 in SEQ ID NO:61 and marker DBSNP243323 in SEQ ID NO:77.

3. The method of claim 2, wherein the method includes screening for and detecting one or more of a T at position 301 of SEQ ID NO:61, T at position 370 of SEQ ID NO:62, T at position 151 of SEQ ID NO:63, G at position 151 of SEQ ID NO:64, A at position 151 of SEQ ID NO:65, G at position 151 of SEQ ID NO:66, C at position 151 of SEQ ID NO:68, A at position 151 of SEQ ID NO:69, G at position 151 of SEQ ID NO:70, T at position 151 of SEQ ID NO:71, G at position 151 of SEQ ID NO:72, A at position 151 of SEQ ID NO:73, T at position 151 of SEQ ID NO:74, G at position 151 of SEQ ID NO:75, G at position 151 of SEQ ID NO:76, or C at position 61 of SEQ ID NO:77 or C at position 90 of SEQ ID NO:100.

4. The method according to claim 1, wherein the detected one or more low fiber content marker allele is (i) from line CL044864 or its lineage, (ii) from line CL065620 or its lineage, (iii) SEQ ID NO:90, or (iv) SEQ ID NO:95.

5. The method according to claim 1, wherein screening for and detecting the presence of one or more low fiber content marker alleles comprises allele-specific polymerase chain reaction (PCR) amplification or nucleic acid sequencing.

6. The method of claim according to claim 1, wherein screening for and detecting the presence of one or more low fiber content marker alleles comprises use of a probe sequence comprising SEQ ID NO:91, SEQ ID NO:92, SEQ ID NO 96, or SEQ ID NO:97.

7. The method of claim 1 for selecting a plant having low fiber content trait, or germplasm thereof, from a population of plants, wherein the method comprises:

a. obtaining a nucleic acid samples from each plant, or germplasm thereof, in a plurality of plants from a population of plants;

b. screening each sample for a nucleic acid comprising the one or more low fiber content marker alleles in accordance with the method of claim 1; and c. selecting one or more plants, or germplasm thereof, from the population identified as having the low fiber content marker allele screened for in step b.

8. A method for producing a *Brassica napus* plant comprising a low fiber content trait, the method comprising:

a. isolating or providing a nucleic acid sample from each of one or more *Brassica napus* plants or germplasm thereof;

b. screening each sample for and detecting the presence of one or more low fiber content nucleic acid marker alleles located within *Brassica napus* chromosome N13 interval between marker DBSNP143552 in SEQ ID NO:1 and marker DBSNP243314 in SEQ ID NO:89, wherein the one or more detected marker alleles comprise one or more of an A at position 220 of SEQ ID NO:1, A at position 101 of SEQ ID NO:2, C at position 61 of SEQ ID NO:3, T at position 151 of SEQ ID NO:4, C at position 151 of SEQ ID NO:5, A at position of 101 of SEQ ID NO:6, C at position 86 of SEQ ID NO:7, C at position 151 of SEQ ID NO:8, G at position 151 of SEQ ID NO:9, G at position 151 of SEQ ID NO:10, G at position 151 of SEQ ID NO:11, T at position 150 of SEQ ID NO:12, C at position 151 of SEQ ID NO:13, C at position 151 of SEQ ID NO:14, G at position 151 of SEQ ID NO:15, T at position 151 of SEQ ID NO:16, C at position 219 of SEQ ID NO:17, T at position 250 of SEQ ID NO:18, A at position 61 of SEQ ID NO:19, G at position 151 of SEQ ID NO:20, T at position 197 of SEQ ID NO:21, G at position 61 of SEQ ID NO:22, A at position 151 of SEQ ID NO:23, T at position 151 of SEQ ID NO:24, T at position 151 of SEQ ID NO:25, C at position 151 of SEQ ID NO:26, G at position 151 of SEQ ID NO:27, C at position 151 of SEQ ID NO:28, A at position 151 of SEQ ID NO:29, G at position 61 of SEQ ID NO:30, A at position 151 of SEQ ID NO:31, C at position 380 of SEQ ID NO:32, T at position 61 of SEQ ID NO:33, C at position 151 of SEQ ID NO:34, A at position 53 of SEQ ID NO:35, C at position 61 of SEQ ID NO:36, T at position 61 of SEQ ID NO:37, T at position 61 of SEQ ID NO:38, A at position 61 of SEQ ID NO:39, T at position 61 of SEQ ID NO:40, C at position 151 of SEQ ID NO:41, A at position 151 of SEQ ID NO:42, T at position 151 of SEQ ID NO:43, T at position 151 of SEQ ID NO:44, T at position 151 of SEQ ID NO:45, G at position 151 of SEQ ID NO:46, G at position 61 of SEQ ID NO:47, A at position 151 of SEQ ID NO:48, G at position 151 of SEQ ID NO:49, G at position 151 of SEQ ID NO:50, T at position 151 of SEQ ID NO:51, G at position 61 of SEQ ID NO:52, T at position 61 of SEQ ID NO:53, T at position 424 of SEQ ID NO:54, C at position 151 of SEQ ID NO:55, C at position 61 of SEQ ID NO:56, T at position 61 of SEQ ID NO:57, T at position 61 of SEQ ID NO:58, A at position 151 of SEQ ID NO:59, C at position 101 of SEQ ID NO:60, T at position 301 of SEQ ID NO:61, T at position 370 of SEQ ID NO:62, T at position 151 of SEQ ID NO:63, G at position 151 of SEQ ID NO:64, A at position 151 of SEQ ID NO:65, G at position 151 of SEQ ID NO:66, G at position 101 of SEQ ID NO:67, C at position 151 of SEQ ID NO:68, A at position 151 of SEQ ID NO:69, G at position 151 of SEQ ID NO:70, T at position 151 of SEQ ID NO:71, G at position 151 of SEQ ID NO:72, A at position 151 of SEQ ID NO:73, T at position 151 of SEQ ID NO:74, G at position 151 of SEQ ID NO:75, G at position 151 of SEQ ID NO:76, C at position 61 of SEQ ID NO:77, G at position 61 of SEQ ID NO:78, A at position 151 of SEQ ID NO:79, G at position 151 of SEQ ID NO:80, C at position 61 of SEQ ID NO:81, A at position 61 of SEQ ID NO:82, T at position 61 of SEQ ID NO:83, G at position 151 of SEQ ID NO:84, A at position 61 of SEQ ID NO:85, G at position 61 of SEQ ID NO:86, T at position 501 OF SEQ ID NO:87, T at position 101 of SEQ ID NO:88, A at position 101 of SEQ ID NO:89, T at position 101 of SEQ ID NO:90, T at position 201 of SEQ ID NO:95, or C at position 90 of SEQ ID NO:100;

c. selecting a first *Brassica napus* plant or germplasm thereof identified as having the one or more low fiber content marker alleles screened for in step b; and d. crossing the first plant selected in step c. with a second plant to produce progeny plants, wherein at least one of the progeny plants comprises the one or more low fiber content marker alleles.

9. The method of claim 8, wherein the first *Brassica napus* plant and the at least one progeny plants comprise a low fiber content marker (i) located within *Brassica napus* chromosome N13 interval flanked by and including base pair position 8978949 (DBSNP02056, SEQ ID NO:92) and base pair position 9375623 (SEQ ID NO: 77), (ii) from line CL044864 or its lineage, (iii) from line CL065620 or its lineage, or (iv) of T at position 301 of SEQ ID NO:61, T at position 370 of SEQ ID NO:62, T at position 151 of SEQ ID NO:63, G at position 151 of SEQ ID NO:64, A at position 151 of SEQ ID NO:65, G at position 151 of SEQ ID NO:66, C at position 151 of SEQ ID NO:68, A at position 151 of SEQ ID NO:69, G at position 151 of SEQ ID NO:70, T at position 151 of SEQ ID NO:71, G at position 151 of SEQ ID NO:72, A at position 151 of SEQ ID NO:73, T at position 151 of SEQ ID NO:74, G at position 151 of SEQ ID NO:75, G at position 151 of SEQ ID NO:76, or C at position 61 of SEQ ID NO:77, T at position 101 of SEQ ID NO:90, T at position 201 of SEQ ID NO:95, or C at position 90 of SEQ ID NO:100.

10. The method according to claim 8, wherein the at least one marker allele is detected using polymerase chain reaction (PCR)-based sequence specific amplification.

11. The method of claim according to claim 8, wherein the method includes screening for and detecting the presence of one or more of the marker alleles comprises use of a probe sequence comprising SEQ ID NO:91, SEQ ID NO:92, SEQ ID NO: 96, SEQ ID NO:97.

* * * * *